US007709605B2

(12) United States Patent
Knopf et al.

(10) Patent No.: US 7,709,605 B2
(45) Date of Patent: May 4, 2010

(54) ACTRII RECEPTOR POLYPEPTIDES, METHODS AND COMPOSITIONS

(75) Inventors: John Knopf, Carlisle, MA (US); Jasbir Seehra, Lexington, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 353 days.

(21) Appl. No.: 11/190,202

(22) Filed: Jul. 25, 2005

(65) Prior Publication Data

US 2006/0068468 A1  Mar. 30, 2006

Related U.S. Application Data

(60) Provisional application No. 60/590,765, filed on Jul. 23, 2004.

(51) Int. Cl.
C07K 14/00 (2006.01)
(52) U.S. Cl. ...................................................... 530/350
(58) Field of Classification Search .................. 530/350
See application file for complete search history.

(56) References Cited

U.S. PATENT DOCUMENTS

| 5,885,794 | A | 3/1999 | Mathews et al. |
| 6,162,896 | A | 12/2000 | Mathews et al. |
| 6,656,475 | B1 | 12/2003 | Lee et al. |
| 6,891,082 | B2 | 5/2005 | Lee et al. |
| 2003/0118556 | A1 | 6/2003 | Kaspar et al. |
| 2007/0184052 | A1 | 8/2007 | Lin et al. |

FOREIGN PATENT DOCUMENTS

| WO | WO-92/20793 | 11/1992 |
| WO | WO-95/10611 | 4/1995 |
| WO | WO-99/06559 | 2/1999 |
| WO | WO-00/43781 | 7/2000 |
| WO | WO-02/085306 | 10/2002 |
| WO | WO 03/006057 A1 | 1/2003 |
| WO | WO 03/072808 A1 | 9/2003 |
| WO | WO 2004/039948 A2 | 5/2004 |
| WO | WO-2005/028517 | 3/2005 |

OTHER PUBLICATIONS

Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Herbert et al (The Dictionary of Immunology, Academic Press, 3rd Edition, London, 1985, pp. 58-59).*
Coleman et al. (Research in Immunology, 1994; 145(1): 33-36).*
Greenspan et al (Nature Biotechnology, 1999, 7:936-937).*
Abaza et al. (Journal of Protein Chemistry, vol. 11, No. 5, 1992, pp. 433-444).*
Gura (Science, 1997, 278: 1041-1042).*
Kaiser (Science, 2006, 313, 1370).*
Burgess et al. (J. Cell Biol. 111:2129-2138, 1990).*
Lazar et al. (Mol. Cell Biol. 8:1247-1252, 1998).*

Donladson et al., "Activin and inhibin binding to the soluble extracellular domain of activin receptor II", Endocrinology 140(4):1760-1766(1999).
Gray et al., "Identification of a binding site on the type II activin receptor for activin and inhibin", Journal of Biological Chemistry, 275(5):3206-3212(2000).
Thompson et al., "Structures of an ActRIIB: activin A complex reveal a novel binding mode for TGF-beta ligand: receptor interactions", EMBO 22(7):1555-1566(2003).
Donaldson et al., Molecular Cloning and Binding Properties of the Human Type II Activin Receptor, Biochemical and Biophysical Research Communications, 184(1):310-316(1992).
Hemmati-Brivanlou et al., "A truncated activin receptor inhibits mesoderm induction and formation of axial structures in *Xenopus* embryos," *Nature*, 359: 609-614 (1992).
Hill et al., "Regulation of Myostatin in Vivo by Growth and Differentiation Factor-Associated Serum Protein-1: A Novel Protein with Protease Inhibitor and Follistatin Domains," *Molecular Endocrinology*, 17(6): 1144-1154 (2003).
Kaspar et al., "Retrograde Viral Delivery of IGF-1 Prolongs Survival in a Mouse ALS Model," *Science*, 301: 839-842 (2003).
Lee et al., "Regulation of myostatin activity and muscle growth," *PNAS*, 98(16): 9306-9311 (2001).
McNally, Elizabeth M., "Powerful Genes—Myostatin Regulation of Human Muscle Mass," *New England Journal of Medicine*, 350(26): 2642-2644 (2004).
Oh et al., "Activin type IIA and IIB receptors mediate Gdf11 signaling in axial vertebral patterning," *Genes & Development*, 16: 2749-2754 (2002).
Schuelke et al., "Myostatin Mutation Associated with Gross Muscle Hypertrophy in a Child," *New England Journal of Medicine*, 350(26): 2682-2688 (2004).
Song et al., "The Type II Activin Receptors Are Essential for Egg Cylinder Growth, Gastrulation, and Rostral Head Development in Mice," *Development Biology*, 213: 157-169 (1999).
Wolfman et al., "Activation of latent myostatin by the BMP-1/tolloid family of metalloproteinases," *PNAS*, 100(26): 15842-15846 (2003).
Ge et al., GDF11 "Forms a Bone Morphogenetic Protein 1-Activated Latent Complex That Can Modulate Nerve Growth Factor-Induced Differentiation of PC12 Cells", Molecular and Cellular Biology, pp. 5846-5858, 2005.
Matzuk et al., "Different phenotypes for mice deficient in either activins or activin receptor type II", Nature, vol. 374 pp. 356-360, 1995.
McPherron et al., "Regulation of Skeletal Muscle Mass in Mice by a Bew TGF-β Superfamily Member", Nature vol. 387, pp. 83-90, 1997.
"Recombinant Human Activin RIIA/Fc Chimera," R&D Systems 340-R2 (Aug. 27, 2003).

(Continued)

*Primary Examiner*—Sean E Aeder
(74) *Attorney, Agent, or Firm*—Ropes & Gray LLP

(57) ABSTRACT

In certain aspects, the present invention provides compositions and methods for modulating (promoting or inhibiting) growth of a tissue, such as bone, cartilage, muscle, fat, and/or neuron. The present invention also provides methods of screening compounds that modulate activity of an ActRII protein and/or an ActRII ligand. The compositions and methods provided herein are useful in treating diseases associated with abnormal activity of an ActRII protein and/or an ActRII ligand.

29 Claims, 17 Drawing Sheets

OTHER PUBLICATIONS

"Recombinant Human Activin RIIA/Fc Chimera," R&D Systems 339-RB/CF(Aug. 27, 2003).

GenBank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).

Hilden, K., et al., "Expression of Type II Activin Receptor Genes During Differentiation of Human K562 Cells and cDNA Cloning of the Human Type IIB Activin Receptor," Blood, vol. 83(8), pp. 2163-2170 (1994).

del Re et al., Reconstitution and Analysis of Soluble Inhibin and Activin Receptor Complexes in a Cell-free System. The Journal of Biological Chemistry. vol. 279, No. 51 pp. 53126-53135 (2004).

Fuller et al., Activin A is an Essential Cofactor for Osteoclast Induction. Biochemical and Biophysical Research Communications vol. 268, pp. 2-7 (2000).

* cited by examiner

Human ActRIIA soluble (extracellular) polypeptide sequence designed as SEQ ID NO: 1 (116 aa).

AILGRSETQECLFFNANWEKDRTNQTGVEPCYGDKDKRRHCFATWKNISGSIEIVKQGC
WLDDINCYDRTDCVEKKDSPEVYFCCCEGNMCNEKFSYFPEM<u>EVTQPTSNPVTPKPP</u>

Figure 1

Human ActRIIB soluble (extracellular) polypeptide sequence designed as SEQ ID NO: 2 (116 aa).

SGRGEAETRECIYYNANWELERTNQSGLERCEGEQDKRLHCYASWANSSGTIELVKKGC

WLDDFNCYDRQECVATEENPQVYFCCCEGNFCNERFTHLPEA<u>GGPEVTYEPPPTAPT</u>

Figure 2

Human ActRIIA precursor sequence designed as SEQ ID NO: 3 (NP_001607, 513 aa).

MGAAAKLAFAVFLISCSSGAILGRSETQECLFFNANWEKDRTNQTGVEPCYGDKDKRRH

CFATWKNISGSIEIVKQGCWLDDINCYDRTDCVEKKDSPEVYFCCCEGNMCNEKFSYFP

EMEVTQPTSNPVTPKPPYYNILLYSLVPLMLIAGIVICAFWVYRHHKMAYPPVLVPTQD

PGPPPPSPLLGLKPLQLLEVKARGRFGCVWKAQLLNEYVAVKIFPIQDKQSWQNEYEVY

SLPGMKHENILQFIGAEKRGTSVDVDLWLITAFHEKGSLSDFLKANVVSWNELCHIAET

MARGLAYLHEDIPGLKDGHKPAISHRDIKSKNVLLKNNLTACIADFGLALKFEAGKSAG

DTHGQVGTRRYMAPEVLEGAINFQRDAFLRIDMYAMGLVLWELASRCTAADGPVDEYML

PFEEEIGQHPSLEDMQEVVVHKKKRPVLRDYWQKHAGMAMLCETIEECWDHDAEARLSA

GCVGERITQMQRLTNIITTEDIVTVVTMVTNVDFPPKESSL

Figure 3

Human ActRIIB precursor sequence designed as SEQ ID NO: 4 (NP_001097, 512 aa).

MTAPWVALALLWGSLWPGSGRGEAETRECIYYNANWELERTNQSGLERCEGEQDKRLHC

YASWANSSGTIELVKKGCWLDDFNCYDRQECVATEENPQVYFCCCEGNFCNERFTHLPE

AGGPEVTYEPPPTAPTLLTVLAYSLLPIGGLSLIVLLAFWMYRHRKPPYGHVDIHEDPG

PPPPSPLVGLKPLQLLEIKARGRFGCVWKAQLMNDFVAVKIFPLQDKQSWQSEREIFST

PGMKHENLLQFIAAEKRGSNLEVELWLITAFHDKGSLTDYLKGNIITWNELCHVAETMS

RGLSYLHEDVPWCRGEGHKPSIAHRDFKSKNVLLKSDLTAVLADFGLAVRFEPGKPPGD

THGQVGTRRYMAPEVLEGAINFQRDAFLRIDMYAMGLVLWELVSRCKAADGPVDEYMLP

FEEEIGQHPSLEELQEVVVHKKMRPTIKDHWLKHPGLAQLCVTIEECWDHDAEARLSAG

CVEERVSLIRRSVNGTTSDCLVSLVTSVTNVDLPPKESSI

Figure 4

Nucleic acid sequence encoding a human ActRIIA soluble (extracellular) polypeptide, designed as SEQ ID NO: 5 (348 bp).

```
Gctatacttggtagatcagaaactcaggagtgtcttttctttaatgctaattgggaaaaagacagaaccaa
tcaaactggtgttgaaccgtgttatggtgacaaagataaacggcggcattgttttgctacctggaagaata
tttctggttccattgaaatagtgaaacaaggttgttggctggatgatatcaactgctatgacaggactgat
tgtgtagaaaaaaaagacagccctgaagtatattttgttgctgtgagggcaatatgtgtaatgaaaagtt
ttcttatttccagagatggaagtcacacagcccacttcaaatccagttacacctaagccaccc
```

Figure 5

Nucleic acid sequence encoding a human ActRIIB soluble (extracellular) polypeptide, designed as SEQ ID NO: 6 (348 bp).

```
Tctgggcgtggggaggctgagacacgggagtgcatctactacaacgccaactgggagctggagcgcaccaa
ccagagcggcctggagcgctgcgaaggcgagcaggacaagcggctgcactgctacgcctcctgggccaaca
gctctggcaccatcgagctcgtgaagaagggctgctggctagatgacttcaactgctacgataggcaggag
tgtgtggccactgaggagaaccccaggtgtacttctgctgctgtgaaggcaacttctgcaacgagcgctt
cactcatttgccagaggctgggggcccggaagtcacgtacgagccaccccgacagcccccacc
```

Figure 6

Nucleic acid sequence encoding a human ActRIIA precursor protein, designed as SEQ ID NO: 7 (nucleotides 164-1705 of NM_001616, 1542 bp).

```
atgggagctgctgcaaagttggcgtttgccgtctttcttatctcctgttcttcaggtgctatacttggtag
atcagaaactcaggagtgtcttttctttaatgctaattgggaaaaagacagaaccaatcaaactggtgttg
aaccgtgttatggtgacaaagataaacggcggcattgttttgctacctggaagaatatttctggttccatt
gaaatagtgaaacaaggttgttggctgatgatatcaactgctatgacaggactgattgtgtagaaaaaaa
agacagccctgaagtatattttgttgctgtgagggcaatatgtgtaatgaaagttttcttatttccag
agatggaagtcacacagcccacttcaaatccagttacacctaagccaccctattacaacatcctgctctat
tccttggtgccacttatgttaattgcggggattgtcatttgtgcatttgggtgtacaggcatcacaagat
ggcctaccctcctgtacttgttccaactcaagacccaggaccacccccaccttctccattactagggttga
aaccactgcagttattagaagtgaaagcaaggggaagatttggttgtgtctggaaagcccagttgcttaac
gaatatgtggctgtcaaaatatttccaatacaggacaaacagtcatggcaaaatgaatacgaagtctacag
tttgcctggaatgaagcatgagaacatattacagttcattggtgcagaaaaacgaggcaccagtgttgatg
tggatctttggctgatcacagcatttcatgaaaagggttcactatcagactttcttaaggctaatgtggtc
tcttggaatgaactgtgtcatattgcagaaaccatggctagaggattggcatatttacatgaggatatacc
tggcctaaaagatggccacaaacctgccatatctcacagggacatcaaagtaaaaatgtgctgttgaaaa
acaacctgacagcttgcattgctgactttggggttggccttaaaatttgaggctggcaagtctgcaggcgat
acccatggacaggttggtacccggaggtacatggctccagaggtattagagggtgctataaacttccaaag
ggatgcattttgaggatagatatgtatgccatgggattagtcctatgggaactggcttctcgctgactg
ctgcagatggacctgtagatgaatacatgttgccatttgaggaggaaattggccagcatccatctcttgaa
gacatgcaggaagttgttgtgcataaaaaaaagaggcctgttttaagagattattggcagaaacatgctgg
aatggcaatgctctgtgaaaccattgaagaatgtgggatcacgacgcagaagccaggttatcagctggat
gtgtaggtgaaagaattacccagatgcagagactaacaaatattattaccacagaggacattgtaacagtg
gtcacaatggtgacaaatgttgactttcctcccaagaatctagtctatga
```

Figure 7

Nucleic acid sequence encoding a human ActRIIB precursor protein, designed as SEQ ID NO: 8 (nucleotides 5-1543 of NM_001106, 1539 bp).

```
atgacggcgccctgggtggccctcgccctcctctggggatcgctgtggcccggctctgggcgtggggaggc
tgagacacgggagtgcatctactacaacgccaactgggagctggagcgcaccaaccagagcggcctggagc
gctgcgaaggcgagcaggacaagcggctgcactgctacgcctcctgggccaacagctctggcaccatcgag
ctcgtgaagaagggctgctggctagatgacttcaactgctacgataggcaggagtgtgtggccactgagga
gaaccccccaggtgtacttctgctgctgtgaaggcaacttctgcaacgagcgcttcactcatttgccagagg
ctgggggcccggaagtcacgtacgagccaccccgacagccccaccctgctcacggtgctggcctactca
ctgctgcccatcggggggccttttccctcatcgtcctgctggccttttggatgtaccggcatcgcaagccccc
ctacggtcatgtggacatccatgaggaccctgggcctccaccaccatcccctctggtgggcctgaagccac
tgcagctgctggagatcaaggctcgggggcgctttggctgtgtctggaaggcccagctcatgaatgactt
gtagctgtcaagatcttcccactccaggacaagcagtcgtggcagagtgaacgggagatcttcagcacacc
tggcatgaagcacgagaacctgctacagttcattgctgccgagaagcgaggctccaacctcgaagtagagc
tgtggctcatcacggccttccatgacaagggctccctcacggattacctcaaggggaacatcatcacatgg
aacgaactgtgtcatgtagcagagacgatgtcacgaggcctctcatacctgcatgaggatgtgccctggtg
ccgtggcgagggccacaagccgtctattgcccacagggactttaaaagtaagaatgtattgctgaagagcg
acctcacagccgtgctggctgactttggcttggctgttcgatttgagccagggaaacctccaggggacacc
cacggacaggtaggcacgagacggtacatggctcctgaggtgctcgagggagccatcaacttccagagaga
tgccttcctgcgcattgacatgtatgccatggggttggtgctgtgggagcttgtgtctcgctgcaaggctg
cagacggacccgtggatgagtacatgctgccctttgaggaagagattggccagcacccttcgttggaggag
ctgcaggaggtggtggtgcacaagaagatgaggcccaccattaaagatcactggttgaaacacccgggcct
ggcccagctttgtgtgaccatcgaggagtgctggaccatgatgcagaggctcgcttgtccgcgggctgtg
tggaggagcgggtgtccctgattcggaggtcggtcaacggcactacctcggactgtctcgtttccctggtg
acctctgtcaccaatgtggacctgcccctaaagagtcaagcatctaa
```

Figure 8

Expression of the Extracellular Domains of ActRIIa and ActRIIb
Basic General features of the Constructs
 Signal sequence: Native, Honey Bee melting or TPA
 Extra cellular domain
 Mutated Fc
 -reduced Fc receptor binding and complement activation
 -increased half life in circulation
Figure 9

Human ActRIIB sequence

Native Signal sequence:

MTAPWVALALLWGSLWPGSSGRGEAETRECIYYNANWELERTNQSGL
ERCEGEQDKRLHCYASWANSSGTIELVKKGCWLDDFNCYDRQECVAT
EENPQVYFCCCEGNFCNERFTHLPEA

HBML signal sequence:

MKFLVNVALVFMVVYISYIYASGRGEAETRECIYYNANWELERTNQSG
LERCEGEQDKRLHCYASWANSSGTIELVKKGCWLDDFNCYDRQECV
ATEENPQVYFCCCEGNFCNERFTHLPEA

TPA signal sequence:

MDAMKRGLCCVLLLCGAVFVSPSGRGEAETRECIYYNANWELERTN
QSGLERCEGEQDKRLHCYASWANSSGTIELVKKGCWLDDFNCYDRQ
ECVATEENPQVYFCCCEGNFCNERFTHLPEA

Figure 10

Human ACtRIIa with native signal sequence:

MGAAAKLAFAVFVISCSSSGAILGRSETQECLFFNANWEKDRTNQTGVEP
CYGDKDKRRHCFATWKNISGSIEIVKQGCWLDDINCYDRTDCVEKKDSP
EVYFCCCEGNMCNEKFSYFPEMEVTQPTSNPVTPKPP

Figure 11

Alignment of human extracellular domains of ActRIIA and ActRIIB

```
RIIA  20   AILGRSETQECLFFNANWEKDRTNQTGVEPCYGDKDKRRHCFATWKNISGSIEIVKQGCWLDD  82
           G +ET+EC+++NANWE +RTNQ+G+E C G++DKR HC+A+W N SG+IE+VK+GCWLDD
RIIB  19   SGRGEAETRECIYYNANWELERTNQSGLERCEGEQDKRLHCYASWANSSGTIELVKKGCWLDD  81

83   INCYDRTDCVEKKDSPEVYFCCCEGNMCNEKFSYFPEMEVTQPTSNPVTPKPP  135
           NCYDR +CV   +++P+VYFCCCEGN CNE+F++ PE   + T  P      P
      82   FNCYDRQECVATEENPQVYFCCCEGNFCNERFTHLPEAGGPEVTYEPPPTAPT  134
```

Figure 14

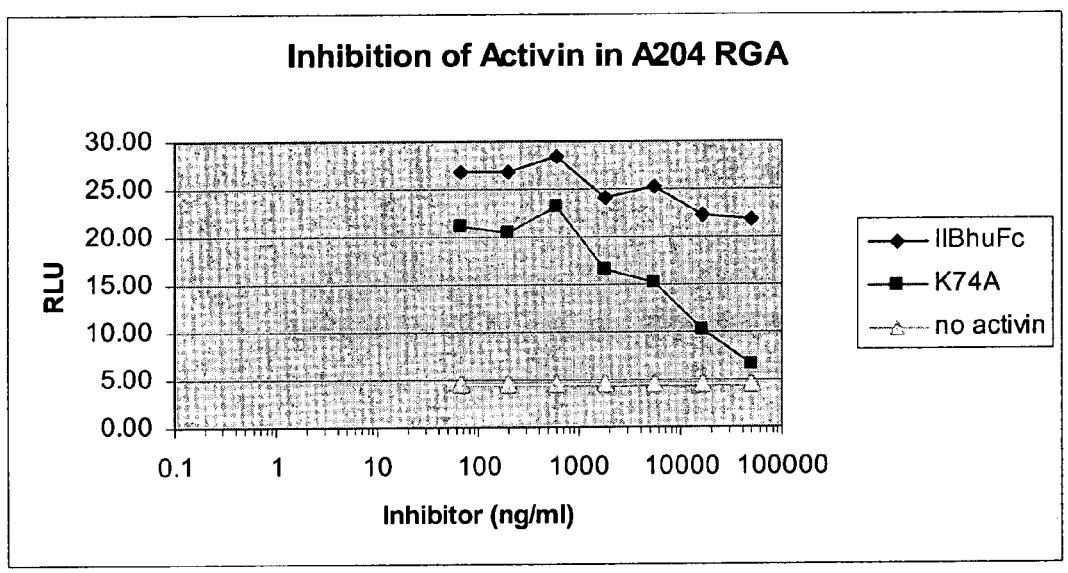

```
SEQUENCE LISTING

<160> NUMBER OF SEQ ID NOS: 19

<210> SEQ ID NO 1
<211> LENGTH: 116
<212> TYPE: PRT
<213> ORGANISM: Homo sapiens

<400> SEQUENCE: 1

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80
```

```
Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Pro Pro
        115

<210> SEQ ID NO 2
<211> LENGTH: 116
<212> TYPE: PRT
<213> ORGANISM: Homo sapiens

<400> SEQUENCE: 2

Ser Gly Arg Gly Glu Ala Glu Thr Arg Glu Cys Ile Tyr Tyr Asn Ala
  1               5                  10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Ala Asn Ser
            35                  40                  45

Ser Gly Thr Ile Glu Leu Val Lys Lys Gly Cys Trp Leu Asp Asp Phe
 50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 3
<211> LENGTH: 513
<212> TYPE: PRT
<213> ORGANISM: Homo sapiens

<400> SEQUENCE: 3

Met Gly Ala Ala Ala Lys Leu Ala Phe Ala Val Phe Leu Ile Ser Cys
  1               5                  10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
 50                  55                  60

Lys Asn Ile Ser Gly Ser Ile Glu Ile Val Lys Gln Gly Cys Trp Leu
 65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160
```

```
Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Trp
1               5                   10                  15
```

-continued

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Ala
            50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                    85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
            130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                    165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
            210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                    245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
            290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                    325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
            370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                    405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
        450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 5
<211> LENGTH: 348
<212> TYPE: DNA
<213> ORGANISM: Homo sapiens

<400> SEQUENCE: 5

| | | | | | |
|---|---|---|---|---|---|
| gctatacttg | gtagatcaga | aactcaggag | tgtcttttct | taatgctaa | ttgggaaaaa | 60 |
| gacagaacca | atcaaactgg | tgttgaaccg | tgttatggtg | acaaagataa | acggcggcat | 120 |
| tgttttgcta | cctggaagaa | tatttctggt | tccattgaaa | tagtgaaaca | aggttgttgg | 180 |
| ctggatgata | tcaactgcta | tgacaggact | gattgtgtag | aaaaaaaaga | cagccctgaa | 240 |
| gtatattttt | gttgctgtga | gggcaatatg | tgtaatgaaa | agttttctta | ttttccagag | 300 |
| atggaagtca | cacagcccac | ttcaaatcca | gttacaccta | agccaccc | | 348 |

<210> SEQ ID NO 6
<211> LENGTH: 348
<212> TYPE: DNA
<213> ORGANISM: Homo sapiens

<400> SEQUENCE: 6

| | | | | | |
|---|---|---|---|---|---|
| tctgggcgtg | gggaggctga | gacacgggag | tgcatctact | acaacgccaa | ctgggagctg | 60 |
| gagcgcacca | accagagcgg | cctggagcgc | tgcgaaggcg | agcaggacaa | gcggctgcac | 120 |
| tgctacgcct | cctgggccaa | cagctctggc | accatcgagc | tcgtgaagaa | gggctgctgg | 180 |
| ctagatgact | tcaactgcta | cgataggcag | gagtgtgtgg | ccactgagga | gaaccccag | 240 |
| gtgtacttct | gctgctgtga | aggcaacttc | tgcaacgagc | gcttcactca | tttgccagag | 300 |
| gctgggggcc | cggaagtcac | gtacgagcca | ccccgacag | ccccccacc | | 348 |

<210> SEQ ID NO 7
<211> LENGTH: 1542
<212> TYPE: DNA
<213> ORGANISM: Homo sapiens

<400> SEQUENCE: 7

| | | | | | |
|---|---|---|---|---|---|
| atgggagctg | ctgcaaagtt | ggcgtttgcc | gtctttctta | tctcctgttc | ttcaggtgct | 60 |
| atacttggta | gatcagaaac | tcaggagtgt | cttttcttta | atgctaattg | ggaaaaagac | 120 |
| agaaccaatc | aaactggtgt | tgaaccgtgt | tatggtgaca | agataaacg | gcggcattgt | 180 |
| tttgctacct | ggaagaatat | ttctggttcc | attgaaatag | tgaaacaagg | ttgttggctg | 240 |
| gatgatatca | actgctatga | caggactgat | tgtgtagaaa | aaaagacag | ccctgaagta | 300 |
| tattttttgtt | gctgtgaggg | caatatgtgt | aatgaaaagt | tttcttattt | tccagagatg | 360 |
| gaagtcacac | agcccacttc | aaatccagtt | acacctaagc | cacccctatta | caacatcctg | 420 |
| ctctattcct | tggtgccact | tatgttaatt | gcggggattg | tcatttgtgc | attttgggtg | 480 |

-continued

| | |
|---|---|
| tacaggcatc acaagatggc ctaccctcct gtacttgttc caactcaaga cccaggacca | 540 |
| ccccacctt ctccattact agggttgaaa ccactgcagt tattagaagt gaaagcaagg | 600 |
| ggaagatttg gttgtgtctg gaaagcccag ttgcttaacg aatatgtggc tgtcaaaata | 660 |
| tttccaatac aggacaaaca gtcatggcaa aatgaatacg aagtctacag tttgcctgga | 720 |
| atgaagcatg agaacatatt acagttcatt ggtgcagaaa aacgaggcac cagtgttgat | 780 |
| gtggatcttt ggctgatcac agcatttcat gaaaagggtt cactatcaga ctttcttaag | 840 |
| gctaatgtgg tctcttggaa tgaactgtgt catattgcag aaaccatggc tagaggattg | 900 |
| gcatatttac atgaggatat acctggccta aagatggcc acaaacctgc catatctcac | 960 |
| agggacatca aaagtaaaaa tgtgctgttg aaaaacaacc tgacagcttg cattgctgac | 1020 |
| tttgggttgg ccttaaaatt tgaggctggc aagtctgcag gcgataccca tggacaggtt | 1080 |
| ggtacccgga ggtacatggc tccagaggta ttagagggtg ctataaactt ccaaagggat | 1140 |
| gcattttga ggatagatat gtatgccatg ggattagtcc tatgggaact ggcttctcgc | 1200 |
| tgtactgctg cagatggacc tgtagatgaa tacatgttgc catttgagga ggaaattggc | 1260 |
| cagcatccat ctcttgaaga catgcaggaa gttgttgtgc ataaaaaaaa gaggcctgtt | 1320 |
| ttaagagatt attggcagaa acatgctgga atggcaatgc tctgtgaaac cattgaagaa | 1380 |
| tgttgggatc acgacgcaga agccaggtta tcagctggat gtgtaggtga aagaattacc | 1440 |
| cagatgcaga gactaacaaa tattattacc acagaggaca ttgtaacagt ggtcacaatg | 1500 |
| gtgacaaatg ttgactttcc tcccaaagaa tctagtctat ga | 1542 |

<210> SEQ ID NO 8
<211> LENGTH: 1539
<212> TYPE: DNA
<213> ORGANISM: Homo sapiens

<400> SEQUENCE: 8

| | |
|---|---|
| atgacggcgc cctgggtggc cctcgccctc ctctggggat cgctgtggcc cggctctggg | 60 |
| cgtggggagg ctgagacacg ggagtgcatc tactacaacg ccaactggga gctggagcgc | 120 |
| accaaccaga gcggcctgga gcgctgcgaa ggcgagcagg acaagcggct gcactgctac | 180 |
| gcctcctggg ccaacagctc tggcaccatc gagctcgtga agaagggctg ctggctagat | 240 |
| gacttcaact gctacgatag caggagtgt gtggccactg aggagaaccc ccaggtgtac | 300 |
| ttctgctgct gtgaaggcaa cttctgcaac gagcgcttca ctcatttgcc agaggctggg | 360 |
| ggcccggaag tcacgtacga gccaccccg acagccccca ccctgctcac ggtgctggcc | 420 |
| tactcactgc tgcccatcgg gggcctttcc ctcatcgtcc tgctggcctt ttggatgtac | 480 |
| cggcatcgca agcccccta cggtcatgtg gacatccatg aggaccctgg gcctccacca | 540 |
| ccatcccctc tggtgggcct gaagccactg cagctgctgg agatcaaggc tcggggcgc | 600 |
| tttggctgtg tctggaaggc ccagctcatg aatgactttg tagctgtcaa gatcttccca | 660 |
| ctccaggaca gcagtcgtg gcagagtgaa cgggagatct tcagcacacc tggcatgaag | 720 |
| cacgagaacc tgctacagtt cattgctgcc gagaagcgag gctccaacct cgaagtagag | 780 |
| ctgtggctca tcacggcctt ccatgacaag ggctcccta cggattacct caaggggaac | 840 |
| atcatcacat ggaacgaact tgtgtcatgta gcagagacga tgtcacgagg cctctctatac | 900 |
| ctgcatgagg atgtgccctg gtgccgtggc gagggccaca agccgtctat tgcccacagg | 960 |
| gactttaaaa gtaagaatgt attgctgaag agcgacctca cagccgtgct ggctgacttt | 1020 |
| ggcttggctg ttcgatttga gccagggaaa cctccagggg acacccacgg acaggtaggc | 1080 |

```
acgagacggt acatggctcc tgaggtgctc gagggagcca tcaacttcca gagagatgcc    1140
ttcctgcgca ttgacatgta tgccatgggg ttggtgctgt gggagcttgt gtctcgctgc    1200
aaggctgcag acggacccgt ggatgagtac atgctgccct ttgaggaaga gattggccag    1260 caccttcgt tggaggagct gcaggaggtg gtggtgcaca agaagatgag gcccaccatt     1320
aaagatcact ggttgaaaca cccgggcctg gcccagcttt gtgtgaccat cgaggagtgc    1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgccccc taaagagtca agcatctaa                           1539
```

<210> SEQ ID NO 9
<211> LENGTH: 119
<212> TYPE: PRT
<213> ORGANISM: Homo sapiens

<400> SEQUENCE: 9

```
Met Thr Ala Pro Trp Val Ala Leu Ala Leu Leu Trp Gly Ser Leu Trp
 1               5                  10                  15

Pro Gly Ser Gly Arg Gly Glu Ala Glu Thr Arg Glu Cys Ile Tyr Tyr
             20                  25                  30

Asn Ala Asn Trp Glu Leu Glu Arg Thr Asn Gln Ser Gly Leu Glu Arg
         35                  40                  45

Cys Glu Gly Glu Gln Asp Lys Arg Leu His Cys Tyr Ala Ser Trp Ala
     50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Cys Glu Gly Asn Phe Cys Asn Glu Arg
            100                 105                 110

Phe Thr His Leu Pro Glu Ala
        115
```

<210> SEQ ID NO 10
<211> LENGTH: 122
<212> TYPE: PRT
<213> ORGANISM: Homo sapiens

<400> SEQUENCE: 10

```
Met Lys Phe Leu Val Asn Val Ala Leu Val Phe Met Val Val Tyr Ile
 1               5                  10                  15

Ser Tyr Ile Tyr Ala Ser Gly Arg Gly Glu Ala Glu Thr Arg Glu Cys
             20                  25                  30

Ile Tyr Tyr Asn Ala Asn Trp Glu Leu Glu Arg Thr Asn Gln Ser Gly
         35                  40                  45

Leu Glu Arg Cys Glu Gly Glu Gln Asp Lys Arg Leu His Cys Tyr Ala
     50                  55                  60

Ser Trp Ala Asn Ser Ser Gly Thr Ile Glu Leu Val Lys Lys Gly Cys
 65                  70                  75                  80

Trp Leu Asp Asp Phe Asn Cys Tyr Asp Arg Gln Glu Cys Val Ala Thr
                 85                  90                  95

Glu Glu Asn Pro Gln Val Tyr Phe Cys Cys Cys Glu Gly Asn Phe Cys
            100                 105                 110

Asn Glu Arg Phe Thr His Leu Pro Glu Ala
```

```
                 115                 120

<210> SEQ ID NO 11
<211> LENGTH: 123
<212> TYPE: PRT
<213> ORGANISM: Homo sapiens

<400> SEQUENCE: 11

Met Asp Ala Met Lys Arg Gly Leu Cys Cys Val Leu Leu Leu Cys Gly
  1               5                  10                  15

Ala Val Phe Val Ser Pro Ser Gly Arg Gly Glu Ala Glu Thr Arg Glu
             20                  25                  30

Cys Ile Tyr Tyr Asn Ala Asn Trp Glu Leu Glu Arg Thr Asn Gln Ser
         35                  40                  45

Gly Leu Glu Arg Cys Glu Gly Glu Gln Asp Lys Arg Leu His Cys Tyr
     50                  55                  60

Ala Ser Trp Ala Asn Ser Ser Gly Thr Ile Glu Leu Val Lys Lys Gly
 65                  70                  75                  80

Cys Trp Leu Asp Asp Phe Asn Cys Tyr Asp Arg Gln Glu Cys Val Ala
                 85                  90                  95

Thr Glu Glu Asn Pro Gln Val Tyr Phe Cys Cys Cys Glu Gly Asn Phe
             100                 105                 110

Cys Asn Glu Arg Phe Thr His Leu Pro Glu Ala
         115                 120

<210> SEQ ID NO 12
<211> LENGTH: 135
<212> TYPE: PRT
<213> ORGANISM: Homo sapiens

<400> SEQUENCE: 12

Met Gly Ala Ala Ala Lys Leu Ala Phe Ala Val Phe Val Ile Ser Cys
  1               5                  10                  15

Ser Ser Gly Ala Ile Leu Gly Arg Ser Glu Thr Gln Glu Cys Leu Phe
             20                  25                  30

Phe Asn Ala Asn Trp Glu Lys Asp Arg Thr Asn Gln Thr Gly Val Glu
         35                  40                  45

Pro Cys Tyr Gly Asp Lys Asp Lys Arg Arg His Cys Phe Ala Thr Trp
     50                  55                  60

Lys Asn Ile Ser Gly Ser Ile Glu Ile Val Lys Gln Gly Cys Trp Leu
 65                  70                  75                  80

Asp Asp Ile Asn Cys Tyr Asp Arg Thr Asp Cys Val Glu Lys Lys Asp
                 85                  90                  95

Ser Pro Glu Val Tyr Phe Cys Cys Cys Glu Gly Asn Met Cys Asn Glu
             100                 105                 110

Lys Phe Ser Tyr Phe Pro Glu Met Glu Val Thr Gln Pro Thr Ser Asn
         115                 120                 125

Pro Val Thr Pro Lys Pro Pro
     130                 135

<210> SEQ ID NO 13
<211> LENGTH: 225
<212> TYPE: PRT
<213> ORGANISM: Homo sapiens
<220> FEATURE:
<221> NAME/KEY: VARIANT
<222> LOCATION: 43
<223> OTHER INFORMATION: Xaa = Asp or Ala
<220> FEATURE:
```

```
<221> NAME/KEY: VARIANT
<222> LOCATION: 100
<223> OTHER INFORMATION: Xaa = Lys or Ala
<220> FEATURE:
<221> NAME/KEY: VARIANT
<222> LOCATION: 212
<223> OTHER INFORMATION: Xaa = Asn or Ala

<400> SEQUENCE: 13

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
            85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Xaa His Tyr Thr Gln Lys Ser Leu Ser Leu Ser Pro Gly
    210                 215                 220

Lys
225

<210> SEQ ID NO 14
<211> LENGTH: 329
<212> TYPE: PRT
<213> ORGANISM: Homo sapiens

<400> SEQUENCE: 14

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65              70                  75                  80

Val Tyr Phe Cys Cys Cys Glu Gly Asn Phe Cys Asn Glu Arg Phe Thr
```

```
                         85                  90                  95
His Leu Pro Glu Ala Gly Gly Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
            130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Val Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 15
<211> LENGTH: 344
<212> TYPE: PRT
<213> ORGANISM: Homo sapiens

<400> SEQUENCE: 15

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
            115                 120                 125
```

```
Pro Glu Leu Leu Gly Gly Pro Ser Val Phe Leu Phe Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 16
<211> LENGTH: 329
<212> TYPE: PRT
<213> ORGANISM: Homo sapiens

<400> SEQUENCE: 16

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160
```

```
Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 17
<211> LENGTH: 344
<212> TYPE: PRT
<213> ORGANISM: Homo sapiens

<400> SEQUENCE: 17

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Pro Pro Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
```

```
                195                 200                 205
Asp Trp Leu Asn Gly Lys Glu Tyr Lys Cys Lys Val Ser Asn Lys Ala
    210                 215                 220
Leu Pro Val Pro Ile Glu Lys Thr Ile Ser Lys Ala Lys Gly Gln Pro
225                 230                 235                 240
Arg Glu Pro Gln Val Tyr Thr Leu Pro Pro Ser Arg Glu Glu Met Thr
                245                 250                 255
Lys Asn Gln Val Ser Leu Thr Cys Leu Val Lys Gly Phe Tyr Pro Ser
            260                 265                 270
Asp Ile Ala Val Glu Trp Glu Ser Asn Gly Gln Pro Glu Asn Asn Tyr
        275                 280                 285
Lys Thr Thr Pro Pro Val Leu Asp Ser Asp Gly Ser Phe Phe Leu Tyr
    290                 295                 300
Ser Lys Leu Thr Val Asp Lys Ser Arg Trp Gln Gln Gly Asn Val Phe
305                 310                 315                 320
Ser Cys Ser Val Met His Glu Ala Leu His Asn His Tyr Thr Gln Lys
                325                 330                 335
Ser Leu Ser Leu Ser Pro Gly Lys
            340

<210> SEQ ID NO 18
<211> LENGTH: 164
<212> TYPE: PRT
<213> ORGANISM: Homo sapiens

<400> SEQUENCE: 18

Ala Ile Leu Gly Arg Ser Glu Thr Gln Glu Cys Leu Phe Phe Asn Ala
1               5                   10                  15
Asn Trp Glu Lys Asp Arg Thr Asn Gln Thr Gly Val Glu Pro Cys Tyr
            20                  25                  30
Gly Asp Lys Asp Lys Arg Arg His Cys Phe Ala Thr Trp Lys Asn Ile
        35                  40                  45
Ser Gly Ser Ile Glu Ile Val Lys Gln Gly Cys Trp Leu Asp Asp Gly
    50                  55                  60
Glu Thr Glu Cys Asn Ala Asn Trp Glu Arg Thr Asn Gln Gly Glu Cys
65                  70                  75                  80
Gly Asp Lys Arg His Cys Ala Trp Asn Ser Gly Ile Glu Val Lys Gly
                85                  90                  95
Cys Trp Leu Asp Asp Ser Gly Arg Gly Glu Ala Glu Thr Arg Glu Cys
            100                 105                 110
Ile Tyr Tyr Asn Ala Asn Trp Glu Leu Glu Arg Thr Asn Gln Ser Gly
        115                 120                 125
Leu Glu Arg Cys Glu Gly Glu Gln Asp Lys Arg Leu His Cys Tyr Ala
    130                 135                 140
Ser Trp Ala Asn Ser Ser Gly Thr Ile Glu Leu Val Lys Lys Gly Cys
145                 150                 155                 160
Trp Leu Asp Asp

<210> SEQ ID NO 19
<211> LENGTH: 132
<212> TYPE: PRT
<213> ORGANISM: Homo sapiens

<400> SEQUENCE: 19

Ile Asn Cys Tyr Asp Arg Thr Asp Cys Val Glu Lys Lys Asp Ser Pro
1               5                   10                  15
```

```
                    -continued

Glu Val Tyr Phe Cys Cys Cys Glu Gly Asn Met Cys Asn Glu Lys Phe
             20              25              30

Ser Tyr Phe Pro Glu Met Glu Val Thr Gln Pro Thr Ser Asn Pro Val
         35              40              45

Thr Pro Lys Pro Pro Asn Cys Tyr Asp Arg Cys Val Pro Val Tyr Phe
     50              55              60

Cys Cys Glu Gly Asn Cys Asn Glu Phe Pro Glu Thr Pro Pro Phe
65              70              75              80

Asn Cys Tyr Asp Arg Gln Glu Cys Val Ala Thr Glu Glu Asn Pro Gln
             85              90              95

Val Tyr Phe Cys Cys Glu Gly Asn Phe Cys Asn Glu Arg Phe Thr
             100             105             110

His Leu Pro Glu Ala Gly Gly Pro Glu Val Thr Tyr Glu Pro Pro Pro
         115             120             125

Thr Ala Pro Thr
     130
```

ACTRII RECEPTOR POLYPEPTIDES, METHODS AND COMPOSITIONS

CROSS-REFERENCE TO RELATED APPLICATIONS

This application claims the benefit of U.S. Provisional Application Ser. No. 60/590,765, filed Jul. 23, 2004. All the teachings of the above-referenced application is incorporated herein by reference.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Changes in muscle, bone, cartilage and other tissues may be achieved by agonizing or antagonizing signaling that is mediated by an appropriate TGF-beta family member. Thus, there is a need for agents that function as potent regulators of TGF-beta signaling.

SUMMARY OF THE INVENTION

In certain aspects, the present disclosure provides ActRII polypeptides. Such ActRII polypeptides may be used for the treatment of a variety of disorders or conditions, in particular, muscle and neuromuscular disorders (e.g., muscular dystrophy, amyotrophic lateral sclerosis (ALS), and muscle atrophy), undesired bone/cartilage growth, adipose tissue disorders (e.g., obesity), metabolic disorders (e.g., type 2 diabetes), and neurodegenerative disorders. In specific embodiments, ActRII polypeptides (e.g., soluble ActRII polypeptides) can antagonize an ActRII receptor (e.g., ActRIIA or ActRIIB) generally, in any process associated with ActRII activity. Optionally, ActRII polypeptides of the invention may be designed to preferentially antagonize one or more ligands of ActRII receptors, such as GDF8 (also called myostatin), GDF11, activin, Nodal, and BMP7 (also called OP-1), and may therefore be useful in the treatment of additional disorders. Examples of ActRII polypeptides include the naturally occurring ActRII polypeptides as well as functional variants thereof.

In certain aspects, the disclosure provides pharmaceutical preparations comprising a soluble ActRII (e.g., ActRIIA or ActRIIB) polypeptide that binds to an ActRII ligand such as GDF8, GDF11, activin, BMP7 or nodal, and a pharmaceutically acceptable carrier. Optionally, the soluble ActRII polypeptide binds to an ActRII ligand with a Kd less than 10 micromolar or less than 1 micromolar, 100, 10 or 1 nanomolar. Optionally, the soluble ActRII polypeptide inhibits ActRII signaling, such as intracellular signal transduction events triggered by an ActRII ligand. A soluble ActRII polypeptide for use in such a preparation may be any of those disclosed herein, such as a polypeptide having an amino acid sequence selected from SEQ ID NOs: 1-2 and 9-12, or having an amino acid sequence that is at least 80%, 85%, 90%, 95%, 97% or 99% identical to an amino acid sequence selected from SEQ ID NOs: 1-2 and 9-12. A soluble ActRII polypeptide may include a functional fragment of a natural ActRII polypeptide, such as one comprising at least 10, 20 or 30 amino acids of a sequence selected from SEQ ID NOs: 1-4 and 9-12 or a sequence of SEQ ID NOs: 1 or 2, lacking the C-terminal 10 to 15 amino acids (the "tail"). A soluble ActRII polypeptide may include one or more alterations in the amino acid sequence (e.g., in the ligand-binding domain) relative to a naturally occurring ActRII polypeptide. The alteration in the amino acid sequence may, for example, alter glycosylation of the polypeptide when produced in a mammalian, insect or other eukaryotic cell or alter proteolytic cleavage of the polypeptide relative to the naturally occurring ActRII polypeptide. A soluble ActRII polypeptide may be a fusion protein that has, as one domain, an ActRII polypeptide (e.g., a ligand-binding domain of an ActRII) and one or more additional domains that provide a desirable property, such as improved pharmacokinetics, easier purification, targeting to particular tissues, etc.

For example, a domain of a fusion protein may enhance one or more of in vivo stability, in vivo half life, uptake/administration, tissue localization or distribution, formation of protein complexes, multimerization of the fusion protein, and/or purification. A soluble ActRII fusion protein may include an immunoglobulin Fc domain (wild-type or mutant) or a serum albumin. In a preferred embodiment, an ActRII-Fc fusion comprises a relatively unstructured linker positioned between the Fc domain and the extracellular ActRII domain. This unstructured linker may correspond to the roughly 15 amino acid unstructured region at the C-terminal end of the extracellular domain of ActRIIA or ActRIIB (the "tail"), or it may be an artificial sequence of between 5 and 15, 20, 30, 50 or more amino acids that are relatively free of secondary structure. A linker may be rich in glycine and proline residues and may, for example, contain repeating sequences of threonine/serine and glycines (e.g., $TG_4$ or $SG_4$ repeats). A fusion protein may include a purification subsequence, such as an epitope tag, a FLAG tag, a polyhistidine sequence, and a GST fusion. Optionally, a soluble ActRII polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat an ActRII-associated disorder. Preferably, a pharmaceutical preparation is substantially pyrogen free. In general, it is preferable that an ActRII protein be expressed in a mammalian cell line that mediates suitably natural glycosylation of the ActRII protein so as to diminish the likelihood of an unfavorable immune response in a patient. Human and CHO cell lines have been used successfully, and it is expected that other common mammalian expression vectors will be useful.

In certain aspects, the disclosure provides packaged pharmaceuticals comprising a pharmaceutical preparation described herein and labeled for use in promoting growth of a tissue or diminishing or preventing a loss of a tissue in a human. Exemplary tissues include bone, cartilage, muscle, fat, and neuron.

In certain aspects, the disclosure provides soluble ActRII polypeptides comprising an altered ligand-binding (e.g., GDF8-binding) domain of an ActRII. Such altered ligand-binding domains of an ActRII receptor comprise one or more mutations at amino acid residues such as E37, E39, R40, K55, R56, Y60, A64, K74, W78, L79, D80, F82 and F101 of human ActRIIB. Such altered ligand-binding domains of an ActRII receptor comprise one or more mutations at amino acid residues such as E38, E40, R41, K56, R57, Y61, K65, K75, W79, L80, D81, I83 and F102 of human ActRIIA. Optionally, the altered ligand-binding domain can have increased selectivity for a ligand such as GDF8/GDF11 relative to a wild-type ligand-binding domain of an ActRII receptor. To illustrate, these mutations are demonstrated herein to increase the selectivity of the altered ligand-binding domain for GDF11 (and therefore, presumably, GDF8) over activin (presented with respect to ActRIIB): K74Y, K74F, K74I and D80I. The following mutations have the reverse effect, increasing the ratio of activin binding over GDF11: D54A, K55A, L79A and F82A. The overall (GDF11 and activin) binding activity can be increased by inclusion of the "tail" region or, presumably, a unstructured linker region, and also by use of a mutation such as A64R (which occurs naturally) or K74A. Other mutations that caused an overall decrease in ligand binding affinity, include: R40A, E37A, R56A, W78A, D80K, D80R, D80A, D80G, D80F, D80M and D80N. Mutations may be combined to achieve desired effects. For example, many of the mutations that affect the ratio of GDF11:Activin binding have an overall negative effect on ligand binding, and therefore, these may be combined with mutations that generally increase ligand binding to produce an improved binding protein with ligand selectivity.

Optionally, the altered ligand-binding domain has a ratio of $K_d$ for activin binding to $K_d$ for GDF8 binding that is at least 2, 5, 10, or even 100 fold greater relative to the ratio for the wild-type ligand-binding domain. Optionally, the altered ligand-binding domain has a ratio of $IC_{50}$ for inhibiting activin to $IC_{50}$ for inhibiting GDF8/GDF11 that is at least 2, 5, 10, or even 100 fold greater relative to the wild-type ligand-binding domain. Optionally, the altered ligand-binding domain inhibits GDF8/GDF11 with an $IC_{50}$ at least 2, 5, 10, or even 100 times less than the $IC_{50}$ for inhibiting activin. These soluble ActRII polypeptides can be fusion proteins that include an immunoglobulin Fc domain (either wild-type or mutant). In certain cases, the subject soluble ActRII polypeptides are antagonists (inhibitors) of GDF8/GDF11.

In certain aspects, the disclosure provides nucleic acids encoding a soluble ActRII polypeptide, which do not encode a complete ActRII polypeptide. An isolated polynucleotide may comprise a coding sequence for a soluble ActRII polypeptide, such as described above. For example, an isolated nucleic acid may include a sequence coding for an extracellular domain (e.g., ligand-binding domain) of an ActRII and a sequence that would code for part or all of the transmembrane domain and/or the cytoplasmic domain of an ActRII, but for a stop codon positioned within the transmembrane domain or the cytoplasmic domain, or positioned between the extracellular domain and the transmembrane domain or cytoplasmic domain. For example, an isolated polynucleotide may comprise a full-length ActRII polynucleotide sequence such as SEQ ID NO: 7 or 8, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRII. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble ActRII polypeptide. Such a method may include expressing any of the nucleic acids (e.g., SEQ ID NO: 5 or 6) disclosed herein in a suitable cell, such as a Chinese hamster ovary (CHO) cell. Such a method may comprise: a) culturing a cell under conditions suitable for expression of the soluble ActRII polypeptide, wherein said cell is transformed with a soluble ActRII expression construct; and b) recovering the soluble ActRII polypeptide so expressed. Soluble ActRII polypeptides may be recovered as crude, partially purified or highly purified fractions using any of the well known techniques for obtaining protein from cell cultures.

In certain aspects, a soluble ActRII polypeptide disclosed herein may be used in a method for treating a subject having a disorder associated with muscle loss or insufficient muscle growth. Such disorders include muscle atrophy, muscular dystrophy, amyotrophic lateral sclerosis (ALS), and a muscle wasting disorder (e.g., cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies). A method may comprise administering to a subject in need thereof an effective amount of a soluble ActRII polypeptide.

In certain aspects, a soluble ActRII polypeptide disclosed herein may be used in a method for treating a subject having a disorder associated with neurodegeneration. Such disorders include Alzheimer's Disease (AD), Parkinson's Disease (PD), Amyotrophic Lateral Sclerosis (ALS), Huntington's disease (HD). A method may comprise administering to a subject in need thereof an effective amount of a soluble ActRII polypeptide.

In certain aspects, a soluble ActRII polypeptide disclosed herein may be used in a method for treating a subject having a disorder associated with abnormal cell growth and differentiation. Such disorders include inflammation, allergy, autoimmune diseases, infectious diseases, and tumors. A method may comprise administering to a subject in need thereof an effective amount of a soluble ActRII polypeptide. A selective activin binding ActRII protein may be particularly useful for treating an activin-dependent cancer, such as ovarian cancer.

In certain aspects, a soluble ActRII polypeptide disclosed herein may be used in a method for decreasing the body fat content or reducing the rate of increase in body fat content, and for treating a disorder associated with undesirable body weight gain, such as obesity, non-insulin dependent diabetes mellitus (NIDDM), cardiovascular disease, cancer, hypertension, osteoarthritis, stroke, respiratory problems, and gall bladder disease. These methods may comprise administering to a subject in need thereof an effective amount of a soluble ActRII polypeptide.

In certain specific aspects, a soluble ActRII polypeptide disclosed herein may be used in a method for treating a disorder associated with abnormal activity of GDF8. Such disorders include metabolic disorders such as type 2 diabetes, impaired glucose tolerance, metabolic syndrome (e.g., syndrome X), and insulin resistance induced by trauma (e.g., burns or nitrogen imbalance); adipose tissue disorders (e.g., obesity); muscular dystrophy (including Duchenne's muscular dystrophy); amyotrophic lateral sclerosis (ALS); muscle atrophy; organ atrophy; frailty; carpal tunnel syndrome; congestive obstructive pulmonary disease; sarcopenia, cachexia and other muscle wasting syndromes; osteoporosis; glucocorticoid-induced osteoporosis; osteopenia; osteoarthritis; osteoporosis-related fractures; low bone mass due to chronic glucocorticoid therapy, premature gonadal failure, androgen suppression, vitamin D deficiency, secondary hyperparathyroidism, nutritional deficiencies, and anorexia nervosa. The method may comprise administering to a subject in need thereof an effective amount of a soluble ActRII polypeptide.

In certain aspects, the disclosure provides a method for identifying an agent that stimulates growth of a tissue such as bone, cartilage, muscle, fat, and neuron. The method comprises: a) identifying a test agent that binds to a ligand-binding domain of an ActRII polypeptide competitively with a soluble ActRII polypeptide; and b) evaluating the effect of the agent on growth of the tissue.

In certain aspects, the disclosure provides methods for antagonizing activity of an ActRII polypeptide or an ActRII ligand (e.g., GDF8, GDF11, activin, BMP7, and Nodal) in a cell. The methods comprise contacting the cell with a soluble ActRII polypeptide. Optionally, the activity of the ActRII polypeptide or the ActRII ligand is monitored by a signaling transduction mediated by the ActRII/ActRII ligand complex, for example, by monitoring cell proliferation. The cells of the methods include an osteoblast, a chondrocyte, a myocyte, an adipocyte, a muscle cell, and a neuronal cell.

In certain aspects, the disclosure provides uses of a soluble ActRII polypeptide for making a medicament for the treatment of a disorder or condition as described herein.

BRIEF DESCRIPTION OF THE DRAWINGS

FIG. 1 shows a human ActRIIA soluble (extracellular) polypeptide sequence (SEQ ID NO: 1). The C-terminal "tail" is underlined.

FIG. 2 shows a human ActRIIB soluble (extracellular) polypeptide sequence (SEQ ID NO: 2). The C-terminal "tail" is underlined.

FIG. 3 shows human ActRIIA precursor protein sequence (SEQ ID NO: 3). The signal peptide is underlined; the extracellular domain is in bold (also referred to as SEQ ID NO: 1); and the potential N-linked glycosylation sites are boxed.

FIG. 4 shows human ActRIIB precursor protein sequence (SEQ ID NO: 4). The signal peptide is underlined; the extracellular domain is in bold (also referred to as SEQ ID NO: 2); and the potential N-linked glycosylation sites are boxed.

FIG. 5 shows a nucleic acid sequence encoding a human ActRIIA soluble (extracellular) polypeptide, designed as SEQ ID NO: 5.

FIG. 6 shows a nucleic acid sequence encoding a human ActRIIB soluble (extracellular) polypeptide, designed as SEQ ID NO: 6.

FIG. 7 shows a nucleic acid sequence encoding human ActRIIA precursor protein, designed as SEQ ID NO: 7.

FIG. 8 shows a nucleic acid sequence encoding human ActRIIB precursor protein, designed as SEQ ID NO: 8.

FIG. 9 shows expression of the extracellular (soluble) domains of ActRIIA or ActRIIB. Constructs expressing human extracellular domains of ActRIIA or ActRIIB were made with all three signal sequences.

FIG. 10 shows three soluble ActRIIB polypeptides with various signal sequences, SEQ ID NOs: 9-11.

FIG. 11 shows one soluble ActRIIA polypeptide with its native signal sequence, SEQ ID NO: 12.

FIG. 14 shows an alignment of the extracellular domains of ActRIIA and ActRIIB, with the positions of mutations that, in ActRIIB, are demonstrated herein to affect ligand binding. The alignment shows that the position of these mutations is conserved in ActRIIA.

FIG. 17 shows the effects of various mutations in ActRIIB-Fc on an Activin A, A-204 Reporter Gene Assay. The background A64 construct showed the least effect on Activin A activity. The K74A mutation caused a substantial increase in Activin A inhibition. A control sample lacking Activin A showed no activity.

DETAILED DESCRIPTION OF THE INVENTION

1. Overview

Figure 12:
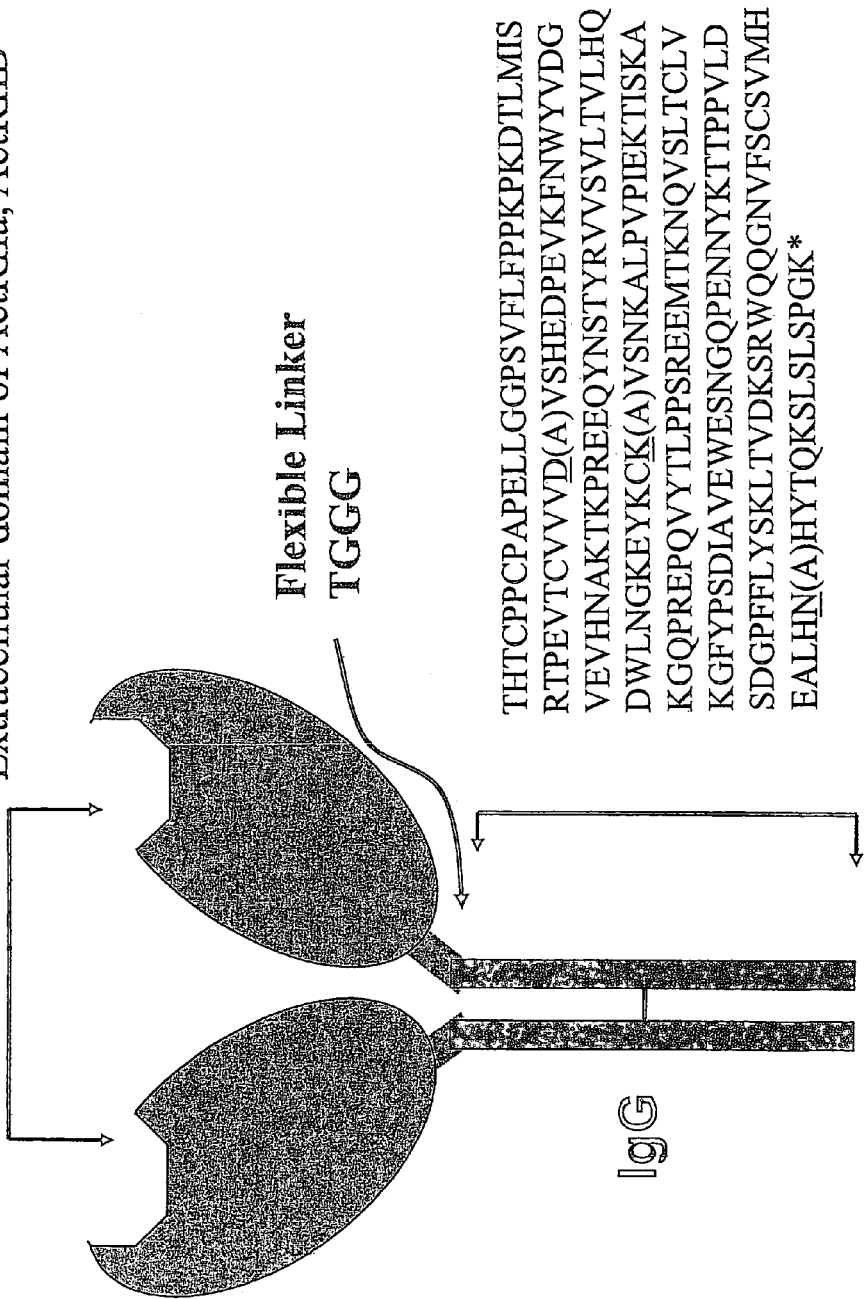
FIG. 12 shows design of the Fc fusions of ActRIIA or ActRIIB polypeptides. The flexible linker sequence and the Fc sequence (SEQ ID NO: 13) are shown. Mutations can be made at one or more amino acid residues of the Fc sequence. Examples of such residues for mutations are underlined, and referred to as Asp-265, lysine-322, and Asn-434.

In certain aspects, the present invention relates to ActRII polypeptides. As used herein, the term "ActRII" refers to a family of activin receptor type II (ActRII) proteins and ActRII-related proteins, derived from any species. Reference to ActRII herein is understood to be a reference to any one of the currently identified forms, including ActRIIA (also known as ActRII) and ActRIIB. Members of the ActRII family are generally all transmembrane proteins, composed of a ligand-binding extracellular domain with cysteine-rich region, a transmembrane domain, and a cytoplasmic domain with predicted serine/threonine kinase specificity. Amino acid sequences of human ActRIIA precursor protein and ActRIIB precursor protein are illustrated in FIG. 3 (SEQ ID NO: 3) and FIG. 4 (SEQ ID NO: 4), respectively.

The term "ActRII polypeptide" is used to refer to polypeptides comprising any naturally occurring polypeptide of an ActRII family member as well as any variants thereof (including mutants, fragments, fusions, and peptidomimetic forms) that retain a useful activity. For example, ActRII polypeptides include polypeptides derived from the sequence of any known ActRII having a sequence at least about 80% identical to the sequence of an ActRII polypeptide, and preferably at least 85%, 90%, 95%, 97%, 99% or greater identity.

In a specific embodiment, the invention relates to soluble ActRII polypeptides. As described herein, the term "soluble ActRII polypeptide" generally refers to polypeptides comprising an extracellular domain of an ActRII protein. The term "soluble ActRII polypeptide," as used herein, includes any naturally occurring extracellular domain of an ActRII protein as well as any variants thereof (including mutants, fragments and peptidomimetic forms) that retain a useful activity. For example, the extracellular domain of an ActRII protein binds to a ligand and is generally soluble. Examples of soluble ActRII polypeptides include ActRIIA and ActRIIB soluble polypeptides illustrated in FIG. 1 (SEQ ID NO: 1) and FIG. 2 (SEQ ID NO: 2), respectively. Other examples of soluble ActRII polypeptides comprise a signal sequence in addition to the extracellular domain of an ActRII protein, for example, the sequences illustrated in FIG. 10 (SEQ ID NOs: 9-11) and FIG. 11 (SEQ ID NO: 12). The signal sequence can be a native signal sequence of an ActRII, or a signal sequence from another protein, such as a tissue plasminogen activator (TPA) signal sequence or a honey bee melatin (HBM) signal sequence.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are all transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54).

In certain embodiments, the present invention relates to antagonizing a ligand of ActRII receptors (also referred to as an ActRII ligand) with a subject ActRII polypeptide (e.g., a soluble ActRII polypeptide). Thus, compositions and methods of the present invention are useful for treating disorders associated with abnormal activity of one or more ligands of ActRII receptors. Exemplary ligands of ActRII receptors include some TGF-β family members, such as activin, Nodal, GDF8, GDF11, and BMP7. These ligands of ActRII receptors are described in more detail below.

Activins are dimeric polypeptide growth factors and belong to the TGF-beta superfamily. There are three activins (A, B, and AB) that are homo/heterodimers of two closely related β subunits ($β_Aβ_A$, $β_Bβ_B$, and $β_Aβ_B$). In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198: 500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $α_2$-macroglobulin, Cerberus, and endoglin, which are described below.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (11999) Dev. Biol., 208: 222-232).

Growth and Differentiation Factor-11 (GDF11), also known as BMP11, is a secreted protein (McPherron et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229: 407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis). Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and IIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different Smad pathways (Macias-Silva et al., 1998, J Biol. Chem. 273:25628-36).

In certain aspects, the present invention relates to the use of certain ActRII polypeptides (e.g., soluble ActRII polypeptides) to antagonize ActRII receptors generally, in any process associated with ActRII activity. Optionally, ActRII polypeptides of the invention may antagonize one or more ligands of ActRII receptors, such as activin, Nodal, GDF8, GDF11, and BMP7, and may therefore be useful in the treatment of additional disorders.

Therefore, the present invention contemplates using ActRII polypeptides in treating or preventing diseases or conditions that are associated with abnormal activity of an ActRII or an ActRII ligand. ActRII or ActRII ligands are involved in the regulation of many critical biological processes. Due to their key functions in these processes, they may be desirable targets for therapeutic intervention. For example, ActRII polypeptides (e.g., e.g., soluble ActRII polypeptides) may be used to treat human or animal disorders or conditions. Example of such disorders or conditions include, but are not limited to, metabolic disorders such as type 2 diabetes, impaired glucose tolerance, metabolic syndrome (e.g., syndrome X), and insulin resistance induced by trauma (e.g., burns or nitrogen imbalance); adipose tissue disorders (e.g., obesity); muscle and neuromuscular disorders such as muscular dystrophy (including Duchenne's muscular dystrophy); amyotrophic lateral sclerosis (ALS); muscle atrophy; organ atrophy; frailty; carpal tunnel syndrome; congestive obstructive pulmonary disease; and sarcopenia, cachexia and other muscle wasting syndromes. Other examples include osteoporosis, especially in the elderly and/or postmenopausal women; glucocorticoid-induced osteoporosis; osteopenia; osteoarthritis; and osteoporosis-related fractures. Yet further examples include low bone mass due to chronic glucocorticoid therapy, premature gonadal failure, androgen suppression, vitamin D deficiency, secondary hyperparathyroidism, nutritional deficiencies, and anorexia nervosa. These disorders and conditions are discussed below under "Exemplary Therapeutic Uses."

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Δ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRII Polypeptides

In certain aspects, the invention relates to ActRII polypeptides (e.g., soluble ActRII polypeptides). Preferably, the fragments, functional variants, and modified forms have similar or the same biological activities of their corresponding wild-type ActRII polypeptides. For example, an ActRII polypeptide of the invention may bind to and inhibit function of an ActRII protein and/or an ActRII ligand protein (e.g., activin, Nodal, GDF8, GDF11 or BMP7). Optionally, an ActRII polypeptide modulates growth of tissues such as bone, cartilage, muscle, fat, and/or neuron. Examples of ActRII polypeptides include human ActRIIA precursor polypeptide (SEQ ID NO: 3), human ActRIIB precursor polypeptide (SEQ ID NO: 4), soluble human ActRIIA polypeptides (e.g., SEQ ID NOs: 1 and 12), soluble human ActRIIB polypeptides (e.g., SEQ ID NOs: 2 and 9-11).

In certain embodiments, isolated fragments of the ActRII polypeptides can be obtained by screening polypeptides recombinantly produced from the corresponding fragment of the nucleic acid encoding an ActRII polypeptide (e.g., one of SEQ ID NOs: 1-2 and 9-12). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of an ActRII protein or an ActRII ligand.

In certain embodiments, a functional variant of the ActRII polypeptides has an amino acid sequence that is at least 75% identical to an amino acid sequence selected from SEQ ID NOs: 1-2 and 9-12. In certain cases, the functional variant has an amino acid sequence at least 80%, 85%, 90%, 95%, 97%, 98%, 99% or 100% identical to an amino acid sequence selected from SEQ ID NOs: 1-2 and 9-12.

In certain embodiments, the present invention contemplates making functional variants by modifying the structure of an ActRII polypeptide for such purposes as enhancing therapeutic efficacy, or stability (e.g., ex vivo shelf life and resistance to proteolytic degradation in vivo). Such modified ActRII polypeptides when designed to retain at least one activity of the naturally-occurring form of the ActRII polypeptides, are considered functional equivalents of the naturally-occurring ActRII polypeptides. Modified ActRII polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRII polypeptide results in a functional homolog can be readily determined by assessing the ability of the variant ActRII polypeptide to produce a response in cells in a fashion similar to the wild-type ActRII polypeptide.

In certain specific embodiments, the present invention contemplates making mutations in the extracellular domain (also referred to as ligand-binding domain) of an ActRII polypeptide such that the variant (or mutant) ActRII polypeptide has altered ligand-binding activities (e.g., binding affinity or binding specificity). In certain cases, such variant ActRII polypeptides have altered (elevated or reduced) binding affinity for a specific ligand. In other cases, the variant ActRII polypeptides have altered binding specificity for their ligands.

Figure 13:
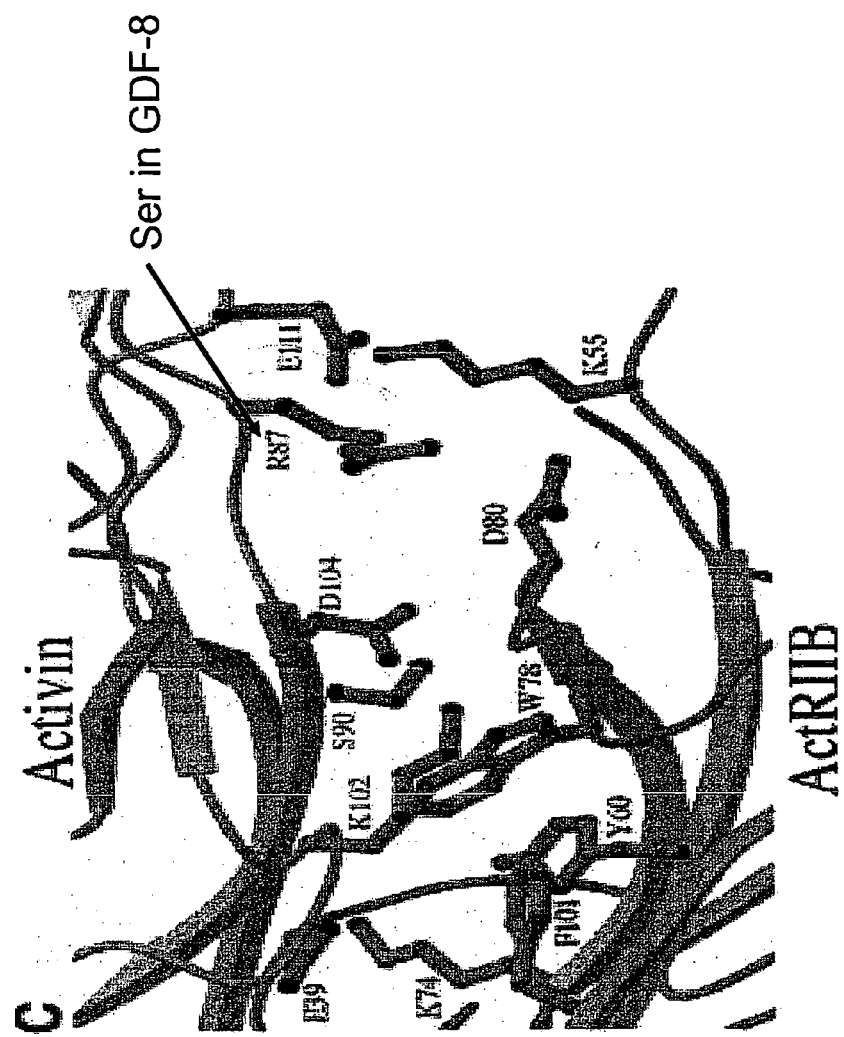
FIG. 13 shows the ligand-binding pocket of an ActRIIB polypeptide. Examples of amino acid residues in the ligand-binding pocket are shown as E39, K55, Y60, K74, W78, D80, and F101. ActRIIB polypeptides of the invention may comprise mutations at one or more of these amino acid residues.
Figure 15:
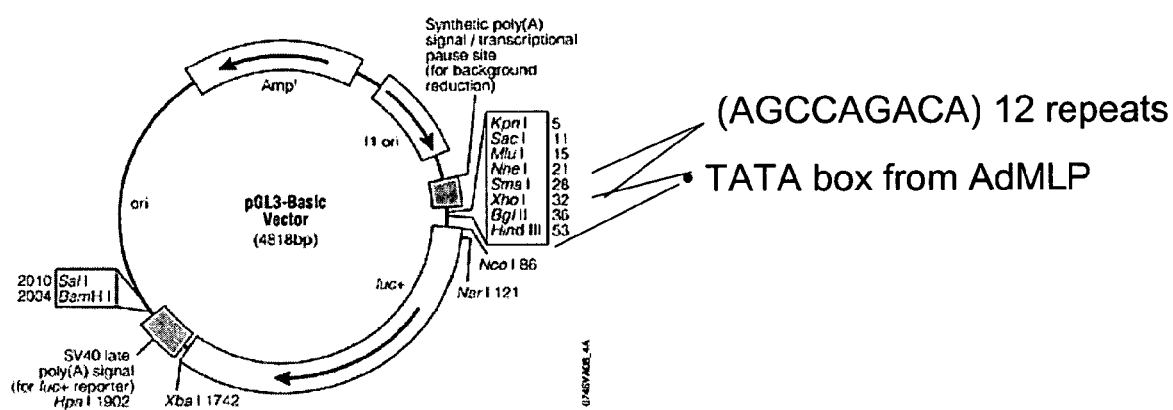
FIG. 15 shows a schematic for the A-204 Reporter Gene Assay. The figure shows the Reporter vector: pGL3(CAGA) 12 (described in Dennler et al, 1998, EMBO 17: 3091-3100.) The CAGA12 motif is present in TGF-Beta responsive genes (PAI-1 gene), so this vector is of general use for factors signaling through Smad2 and 3.
Figure 16:
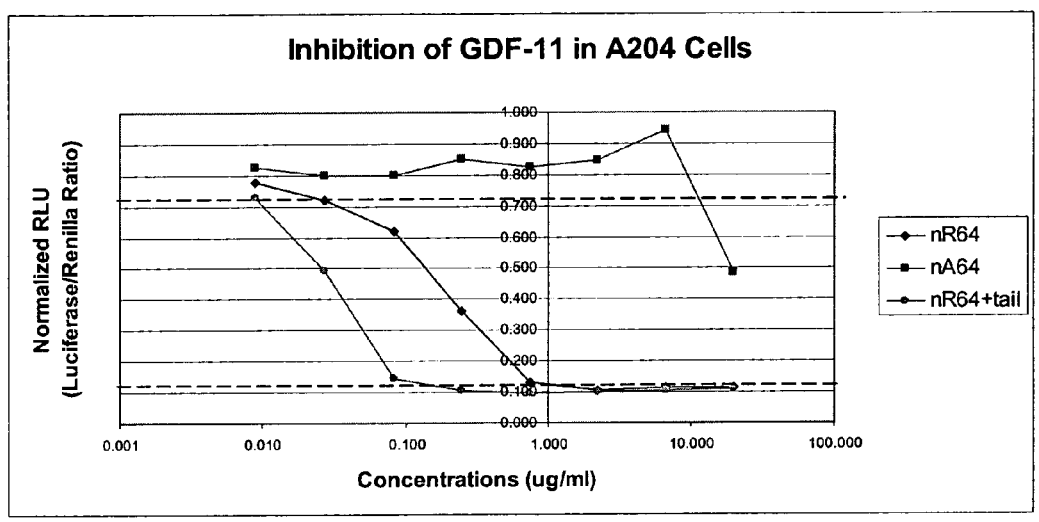
FIG. 16 shows the effects of various mutations in ActRIIB-Fc on a GDF-11 A-204 Reporter Gene Assay. The background A64 construct showed the least effect on GDF-11 activity. The A64K mutation (also a naturally occurring form) caused a substantial increase in GDF-11 inhibition, and a combination of the A64K mutation with the addition of the 15 C-terminal amino acids of the extracellular domain (the 15 amino acid "tail") produced an even more potent inhibitor of GDF-11 activity.

For example, the variant ActRII polypeptide preferentially binds to a specific ligand (e.g., GDF8). For example, amino acid residues of the ActRIIB protein, such as E39, K55, Y60, K74, W78, D80, and F101 (shown in FIG. 13), are in the ligand-binding pocket and mediate binding to its ligands such as activin and GDF8. Thus, the present invention provides an altered ligand-binding domain (e.g., GDF8-binding domain) of an ActRII receptor, which comprises one or more mutations at those amino acid residues. Optionally, the altered ligand-binding domain can have increased selectivity for a ligand such as GDF8 relative to a wild-type ligand-binding domain of an ActRII receptor. To illustrate, these mutations increase the selectivity of the altered ligand-binding domain for GDF8 over activin. Optionally, the altered ligand-binding domain has a ratio of $K_d$ for activin binding to $K_d$ for GDF8 binding that is at least 2, 5, 10, or even 100 fold greater relative to the ratio for the wild-type ligand-binding domain. Optionally, the altered ligand-binding domain has a ratio of $IC_{50}$ for inhibiting activin to $IC_{50}$ for inhibiting GDF8 that is at least 2, 5, 10, or even 100 fold greater relative to the wild-type ligand-binding domain. Optionally, the altered ligand-binding domain inhibits GDF8 with an $IC_{50}$ at least 2, 5, 10, or even 100 times less than the $IC_{50}$ for inhibiting activin.

As an specific example, the positively-charged amino acid residue Asp (D80) of the ligand-binding domain of ActRIIB can be mutated to a different amino acid residue such that the variant ActRII polypeptide preferentially binds to GDF8, but not activin. Preferably, the D60 residue is changed to an amino acid residue selected from the group consisting of: an uncharged amino acid residue, a negative amino acid residue, and a hydrophobic amino acid residue. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates specific mutations of the ActRII polypeptides so as to alter the glycosylation of the polypeptide. Exemplary glycosylation sites in ActRIIA and ActRIIB polypeptides are illustrated in FIGS. 3 and 4 respectively. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRII polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRII polypeptide is by chemical or enzymatic coupling of glycosides to the ActRII polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRII polypeptide may be accomplished chemically and/or enzymatically. Chemical deglycosylation may involve, for example, exposure of the ActRII polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRII polypeptides can be achieved by the use of a variety of endo- and exo-glycosidases as described by Thotakura et al. (1987) Meth. Enzymol. 138:350. The sequence of an ActRII polypeptide may be adjusted, as appropriate, depending on the type of expression system used, as mammalian, yeast, insect and plant cells may all introduce differing glycosylation patterns that can be affected by the amino acid sequence of the peptide. In general, ActRII proteins for use in humans will be expressed in a mammalian cell line that provides proper glycosylation, such as HEK293 or CHO cell lines, although other mammalian expression cell lines are expected to be useful as well.

This disclosure further contemplates a method of generating mutants, particularly sets of combinatorial mutants of an ActRII polypeptide, as well as truncation mutants; pools of combinatorial mutants are especially useful for identifying functional variant sequences. The purpose of screening such combinatorial libraries may be to generate, for example, ActRII polypeptide variants which can act as either agonists or antagonist, or alternatively, which possess novel activities all together. A variety of screening assays are provided below, and such assays may be used to evaluate variants. For example, an ActRII polypeptide variant may be screened for ability to bind to an ActRII polypeptide, to prevent binding of an ActRII ligand to an ActRII polypeptide.

The activity of an ActRII polypeptide or its variants may also be tested in a cell-based or in vivo assay. For example, the effect of an ActRII polypeptide variant on the expression of genes involved in bone production in an osteoblast or precursor may be assessed. This may, as needed, be performed in the presence of one or more recombinant ActRII ligand protein (e.g., BMP7), and cells may be transfected so as to produce an ActRII polypeptide and/or variants thereof, and optionally, an ActRII ligand. Likewise, an ActRII polypeptide may be administered to a mouse or other animal, and one or more bone properties, such as density or volume may be assessed. The healing rate for bone fractures may also be evaluated. Similarly, the activity of an ActRII polypeptide or its variants may be tested in muscle cells, adipocytes, and neuron cells for any effect on growth of these cells, for example, by the assays as described below. Such assays are well known and routine in the art.

Combinatorially-derived variants can be generated which have a selective potency relative to a naturally occurring ActRII polypeptide. Such variant proteins, when expressed from recombinant DNA constructs, can be used in gene therapy protocols. Likewise, mutagenesis can give rise to variants which have intracellular half-lives dramatically different than the corresponding a wild-type ActRII polypeptide. For example, the altered protein can be rendered either more stable or less stable to proteolytic degradation or other cellular processes which result in destruction of, or otherwise inactivation of a native ActRII polypeptide. Such variants, and the genes which encode them, can be utilized to alter ActRII polypeptide levels by modulating the half-life of the ActRII polypeptides. For instance, a short half-life can give rise to more transient biological effects and, when part of an inducible expression system, can allow tighter control of recombinant ActRII polypeptide levels within the cell.

In a preferred embodiment, the combinatorial library is produced by way of a degenerate library of genes encoding a library of polypeptides which each include at least a portion of potential ActRII polypeptide sequences. For instance, a mixture of synthetic oligonucleotides can be enzymatically ligated into gene sequences such that the degenerate set of potential ActRII polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRII polypeptide variants (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218: 597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRII polypeptides. In a specific embodiment, similar methods can be used for making soluble forms of ActRII polypeptides, which can act as agonists or antagonists of ActRII functions.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the ActRII polypeptides of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the ActRII polypeptides.

To illustrate, by employing scanning mutagenesis to map the amino acid residues of an ActRII polypeptide which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the ActRII polypeptides of the invention may further comprise post-translational modifications in addition to any that are naturally present in the ActRII polypeptides. Such modifications include, but are not limited to, acetylation, carboxylation, glycosylation, phosphorylation, lipidation, and acylation. As a result, the modified ActRII polypeptides may contain non-amino acid elements, such as polyethylene glycols, lipids, poly- or mono-saccharide, and phosphates. Effects of such non-amino acid elements on the functionality of a ActRII polypeptide may be tested as described herein for other ActRII polypeptide variants. When an ActRII polypeptide is produced in cells by cleaving a nascent form of the ActRII polypeptide, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the ActRII polypeptides.

In certain aspects, functional variants or modified forms of the ActRII polypeptides include fusion proteins having at least a portion of the ActRII polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ActRII polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRII polypeptide is fused with a domain that stabilizes the ActRII polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As a specific example, the present invention provides a fusion protein as a GDF8 antagonist which comprises an extracellular (e.g., GDF8-binding) domain fused to an Fc domain (e.g., SEQ ID NO: 13).

```
THTCPPCPAPELLGGPSVFLFPPKPKDTLMISRTPEVTCVVVD(A)VSHEDPEVKFNWYVDG

VEVHNAKTKPREEQYNSTYRVVSVLTVLHQDWLNGKEYKCK(A)VSNKALPVPIEKTISKAK

GQPREPQVYTLPPSREEMTKNQVSLTCLVKGFYPSDIAVEWESNGQPENNYKTTPPVLDSDG

PFFLYSKLTVDKSRWQQGNVFSCSVMHEALHN(A)HYTQKSLSLSPGK*
```

Preferably, the Fc domain has one or more mutations at residues such as Asp-265, lysine 322, and Asn-434 (see FIG. 12). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ActRII polypeptide may be placed C-terminal to a heterologous domain, or, alternatively, a heterologous domain may be placed C-terminal to an ActRII polypeptide. The ActRII polypeptide domain and the heterologous domain need not be adjacent in a fusion protein, and additional domains or amino acid sequences may be included C- or N-terminal to either domain or between the domains.

In certain embodiments, the ActRII polypeptides of the present invention contain one or more modifications that are capable of stabilizing the ActRII polypeptides. For example, such modifications enhance the in vitro half life of the ActRII polypeptides, enhance circulatory half life of the ActRII polypeptides or reducing proteolytic degradation of the ActRII polypeptides. Such stabilizing modifications include, but are not limited to, fusion proteins (including, for example, fusion proteins comprising an ActRII polypeptide and a stabilizer domain), modifications of a glycosylation site (including, for example, addition of a glycosylation site to an ActRII polypeptide), and modifications of carbohydrate moiety (including, for example, removal of carbohydrate moieties from an ActRII polypeptide). In the case of fusion proteins, an ActRII polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the ActRII polypeptides, which are isolated from, or otherwise substantially free of, other proteins.

In certain embodiments, ActRII polypeptides (unmodified or modified) of the invention can be produced by a variety of art-known techniques. For example, such ActRII polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W.H. Freeman and Company, New York (1992). In addition, automated peptide synthesizers are commercially available (e.g., Advanced ChemTech Model 396; Milligen/Biosearch 9600). Alternatively, the ActRII polypeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified ActRII polypeptides may be produced by digestion of naturally occurring or recombinantly produced full-length ActRII polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such ActRII polypeptides may be produced from naturally occurring or recombinantly produced full-length ActRII polypeptides such as standard techniques known in the art, such as by chemical cleavage (e.g., cyanogen bromide, hydroxylamine).

3. Nucleic Acids Encoding ActRII Polypeptides

In certain aspects, the invention provides isolated and/or recombinant nucleic acids encoding any of the ActRII polypeptides (e.g., soluble ActRII polypeptides), including fragments, functional variants and fusion proteins disclosed herein. For example, SEQ ID NOs: 7-8 encode naturally occurring ActRII precursor polypeptides, while SEQ ID NOs: 5-6 encode soluble ActRII polypeptides. The subject nucleic acids may be single-stranded or double stranded. Such nucleic acids may be DNA or RNA molecules. These nucleic acids are may be used, for example, in methods for making ActRII polypeptides or as direct therapeutic agents (e.g., in a gene therapy approach).

In certain aspects, the subject nucleic acids encoding ActRII polypeptides are further understood to include nucleic acids that are variants of SEQ ID NO: 7 or 8. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 7 or 8.

In certain embodiments, the invention provides isolated or recombinant nucleic acid sequences that are at least 80%, 85%, 90%, 95%, 97%, 98%, 99% or 100% identical to SEQ ID NO: 5 or 6. One of ordinary skill in the art will appreciate that nucleic acid sequences complementary to SEQ ID NO: 5 or 6, and variants of SEQ ID NO: 5 or 6 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 5 or 6, complement sequence of SEQ ID NO: 5 or 6, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 5-6 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRII polypeptide and operably linked to at least one regulatory sequence. Regulatory sequences are art-recognized and are selected to direct expression of the ActRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRII polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRII polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 7 or 8) for one or more of the subject ActRII polypeptides. The host cell may be any prokaryotic or eukaryotic cell. For example, an ActRII polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ActRII polypeptides. For example, a host cell transfected with an expression vector encoding an ActRII polypeptide can be cultured under appropriate conditions to allow expression of the ActRII polypeptide to occur. The ActRII polypeptide may be secreted and isolated from a mixture of cells and medium containing the ActRII polypeptide. Alternatively, the ActRII polypeptide may be retained cytoplasmically or in a membrane fraction and the cells harvested, lysed and the protein isolated. A cell culture includes host cells, media and other byproducts. Suitable media for cell culture are well known in the art. The subject ActRII polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRII polypeptides. In a preferred embodiment, the ActRII polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant ActRII polypeptide, can allow purification of the expressed fusion protein by affinity chromatography using a $Ni^{2+}$ metal resin. The purification leader sequence can then be subsequently removed by treatment with enterokinase to provide the purified ActRII polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Antibodies

Another aspect of the invention pertains to antibodies. An antibody that is specifically reactive with an ActRII polypeptide (e.g., a soluble ActRII polypeptide) and which binds competitively with the ActRII polypeptide may be used as an antagonist of ActRII polypeptide activities. For example, by using immunogens derived from an ActRII polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRII polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRII polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRII polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRII polypeptide and monoclonal antibodies isolated from a culture comprising such hybridoma cells.

The term "antibody" as used herein is intended to include fragments thereof which are also specifically reactive with a subject ActRII polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an ActRII polypeptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to an ActRII polypeptide may comprise administering to a mouse an amount of an immunogenic composition comprising the ActRII polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the ActRII polypeptide. Once obtained, a hybridoma can be propagated in a cell culture, optionally in culture conditions where the hybridoma-derived cells produce the monoclonal antibody that binds specifically to the ActRII polypeptide. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRII polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain aspects, the disclosure provides antibodies that bind to a soluble ActRII polypeptide. Such antibodies may be generated much as described above, using a soluble ActRII polypeptide or fragment thereof as an antigen. Antibodies of this type can be used, e.g., to detect ActRII polypeptides in biological samples and/or to monitor soluble ActRII polypeptide levels in an individual. In certain cases, an antibody that specifically binds to a soluble ActRII polypeptide can be used to modulate activity of an ActRII polypeptide and/or an ActRII ligand, thereby regulating (promoting or inhibiting) growth of tissues, such as bone, cartilage, muscle, fat, and neurons.

5. Screening Assays

In certain aspects, the present invention relates to the use of the subject ActRII polypeptides (e.g., soluble ActRII polypeptides) to identify compounds (agents) which are agonist or antagonists of the ActRII polypeptides. Compounds identified through this screening can be tested in tissues such as bone, cartilage, muscle, fat, and/or neurons, to assess their ability to modulate tissue growth in vitro. Optionally, these compounds can further be tested in animal models to assess their ability to modulate tissue growth in vivo.

There are numerous approaches to screening for therapeutic agents for modulating tissue growth by targeting the ActRII polypeptides. In certain embodiments, high-throughput screening of compounds can be carried out to identify agents that perturb ActRII-mediated effects on growth of bone, cartilage, muscle, fat, and/or neuron. In certain embodiments, the assay is carried out to screen and identify compounds that specifically inhibit or reduce binding of an ActRII polypeptide to its binding partner, such as an ActRII ligand (e.g., activin, Nodal, GDF8, GDF11 or BMP7). Alternatively, the assay can be used to identify compounds that enhance binding of an ActRII polypeptide to its binding protein such as an ActRII ligand. In a further embodiment, the compounds can be identified by their ability to interact with an ActRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include nonpeptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRII polypeptide and its binding protein (e.g., an ActRII ligand).

Merely to illustrate, in an exemplary screening assay of the present invention, the compound of interest is contacted with an isolated and purified ActRII polypeptide which is ordinarily capable of binding to an ActRII ligand, as appropriate for the intention of the assay. To the mixture of the compound and ActRII polypeptide is then added a composition containing an ActRII ligand. Detection and quantification of ActRII/ActRII ligand complexes provides a means for determining the compound's efficacy at inhibiting (or potentiating) complex formation between the ActRII polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRII ligand is added to a composition containing the ActRII polypeptide, and the formation of ActRII/ActRII ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRII polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRII polypeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRII polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRII polypeptide and its binding protein. See for example, U.S. Pat. No. 5,283,317; Zervos et al. (1993) Cell 72:223-232; Madura et al. (1993) J Biol Chem 268: 12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRII polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRII polypeptide of the invention. The interaction between the compound and the ActRII polypeptide may be covalent or non-covalent. For example, such interaction can be identified at the protein level using in vitro biochemical methods, including photocrosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an ActRII polypeptide. This may include a solid phase or fluid phase binding event. Alternatively, the gene encoding an ActRII polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for stimulating muscle growth and increasing muscle mass, for example, by antagonizing functions of an ActRII polypeptide and/or an ActRII ligand. Therefore, any compound identified can be tested in whole cells or tissues, in vitro or in vivo, to confirm their ability to modulate muscle growth. Various methods known in the art can be utilized for this purpose. For example, methods of the invention are performed such that the signal transduction through an ActRII protein activated by binding to an ActRII ligand (e.g., GDF8) has been reduced or inhibited. It will be recognized that the growth of muscle tissue in the organism would result in an increased muscle mass in the organism as compared to the muscle mass of a corresponding organism (or population of organisms) in which the signal transduction through an ActRII protein had not been so effected.

For example, the effect of the ActRII polypeptides or test compounds on muscle cell growth/proliferation can be determined by measuring gene expression of Pax-3 and Myf-5 which are associated with proliferation of myogenic cells, and gene expression of MyoD which is associated with muscle differentiation (e.g., Amthor et al., Dev Biol. 2002, 251:241-57). It is known that GDF8 down-regulates gene expression of Pax-3 and Myf-5, and prevents gene expression of MyoD. The ActRII polypeptides or test compounds are expected to antagonize this activity of GDF8. Another example of cell-based assays includes measuring the proliferation of myoblasts such as C(2)C(12) myoblasts in the presence of the ActRII polypeptides or test compounds (e.g., Thomas et al., J Biol. Chem. 2000, 275:40235-43).

The present invention also contemplates in vivo assays to measure muscle mass and strength. For example, Whittemore et al. (Biochem Biophys Res Commun. 2003, 300:965-71) discloses a method of measuring increased skeletal muscle mass and increased grip strength in mice. Optionally, this method can be used to determine therapeutic effects of test compounds (e.g., ActRII polypeptides) on muscle diseases or conditions, for example those diseases for which muscle mass is limiting.

In certain aspects, the present invention provides methods and agents for modulating (stimulating or inhibiting) bone formation and increasing bone mass. Therefore, any compound identified can be tested in whole cells or tissues, in vitro or in vivo, to confirm their ability to modulate bone or cartilage growth. Various methods known in the art can be utilized for this purpose.

For example, the effect of the ActRII polypeptides or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the subject ActRII polypeptides and test compounds in mesenchymal progenitor and osteoblastic cells. To illustrate, recombinant adenoviruses expressing an ActRII polypeptide were constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8):1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

In certain aspects, the present invention provides methods and agents for controlling weight gain and obesity. At the cellular level, adipocyte proliferation and differentiation is critical in the development of obesity, which leads to the generation of additional fat cells (adipocytes). Therefore, any compound identified can be tested in whole cells or tissues, in vitro or in vivo, to confirm their ability to modulate adipogenesis by measuring adipocyte proliferation or differentiation. Various methods known in the art can be utilized for this purpose. For example, the effect of an ActRII polypeptide (e.g., a soluble ActRII polypeptide) or test compounds on adipogenesis can be determined by measuring differentiation of 3T3-L1 preadipocytes to mature adipocytes in cell based assays, such as, by observing the accumulation of triacylglycerol in Oil Red O staining vesicles and by the appearance of certain adipocyte markers such as FABP (aP2/422) and PPARγ2. See, for example, Reusch et al., 2000, Mol Cell Biol. 20:1008-20; Deng et al., 2000, Endocrinology. 141:2370-6; Bell et al., 2000, Obes Res. 8:249-54. Another example of cell-based assays includes analyzing the role of ActRII. polypeptides and test compounds in proliferation of adipocytes or adipocyte precursor cells (e.g., 3T3-L1 cells), such as, by monitoring bromodeoxyuridine (BrdU)-positive cells. See, for example, Pico et al., 1998, Mol Cell Biochem. 189: 1-7; Masuno et al., 2003, Toxicol Sci. 75:314-20.

It is understood that the screening assays of the present invention apply to not only the subject ActRII polypeptides and variants of the ActRII polypeptides, but also any test compounds including agonists and antagonist of the ActRII polypeptides. Further, these screening assays are useful for drug target verification and quality control purposes.

6. Exemplary Therapeutic Uses

In certain embodiments, compositions (e.g., ActRII polypeptides) of the present invention can be used for treating or preventing a disease or condition that is associated with abnormal activity of an ActRII polypeptide and/or an ActRII ligand (e.g., GDF8). These diseases, disorders or conditions are generally referred to herein as "ActRII-associated conditions." In certain embodiments, the present invention provides methods of treating or preventing an individual in need thereof through administering to the individual a therapeutically effective amount of an ActRII polypeptide as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

ActRII/ActRII ligand complexes play essential roles in tissue growth as well as early developmental processes such as the correct formation of various structures or in one or more post-developmental capacities including sexual development, pituitary hormone production, and creation of bone and cartilage. Thus, ActRII-associated conditions include abnormal tissue growth and developmental defects. In addition, ActRII-associated conditions include, but are not limited to, disorders of cell growth and differentiation such as inflammation, allergy, autoimmune diseases, infectious diseases, and tumors.

Exemplary ActRII-associated conditions include neuromuscular disorders (e.g., muscular dystrophy and muscle atrophy), congestive obstructive pulmonary disease, muscle wasting syndrome, sarcopenia, cachexia, adipose tissue disorders (e.g., obesity), type 2 diabetes, and bone degenerative disease (e.g., osteoporosis). Other exemplary ActRII-associated conditions include musculodegenerative and neuromuscular disorders, tissue repair (e.g., wound healing), neurodegenerative diseases (e.g., amyotrophic lateral sclerosis), immunologic disorders (e.g., disorders related to abnormal proliferation or function of lymphocytes), and obesity or disorders related to abnormal proliferation of adipocytes.

In certain embodiments, compositions (e.g., soluble ActRII polypeptides) of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject ActRII polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy- (MMD) (also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, recent researches demonstrate that blocking or eliminating function of GDF8 (an ActRII ligand) in vivo can effectively treat at least certain symptoms in DMD and BMD patients (Bogdanovich et al., supra; Wagner et al., supra). Thus, the subject ActRII polypeptides may act as GDF8 inhibitors (antagonists), and constitute an alternative means of blocking the functions of GDF8 and/or ActRII in vivo in DMD and BMD patients.

Similarly, the subject ActRII polypeptides provide an effective means to increase muscle mass in other disease conditions that are in need of muscle growth. For example, Gonzalez-Cadavid et al. (supra) reported that that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 (an ActRII ligand) function is also associated with fat loss without diminution of nutrient intake (Zimmers et al., supra; McPherron and Lee, supra), the subject ActRII polypeptides may further be used as a therapeutic agent for slowing or preventing the development of obesity and type II diabetes.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process. Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of GDF8 in adult mice was found to induce profound muscle and fat loss analogous to that seen in human cachexia syndromes (Zimmers et al., supra), the subject ActRII polypeptides as pharmaceutical compositions can be beneficially used to prevent, treat, or alleviate the symptoms of the cachexia syndrome, where muscle growth is desired.

In other embodiments, the present invention provides methods of inducing bone and/or cartilage formation, preventing bone loss, increasing bone mineralization or preventing the demineralization of bone. For example, the subject ActRII polypeptides and compounds identified in the present invention have application in treating osteoporosis and the healing of bone fractures and cartilage defects in humans and other animals. ActRII polypeptides may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject ActRII polypeptides may provide an environment to attract bone-forming cells, stimulate growth of bone-forming cells or induce differentiation of progenitors of bone-forming cells. ActRII polypeptides of the invention may also be useful in the treatment of osteoporosis. Further, ActRII polypeptides may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the ActRII polypeptides of the invention in admixture with a pharmaceutically acceptable vehicle, carrier or matrix.

In another specific embodiment, methods and compositions of the invention can be applied to conditions causing bone loss such as osteoporosis, hyperparathyroidism, Cushing's disease, thyrotoxicosis, chronic diarrheal state or malabsorption, renal tubular acidosis, or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenyloin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anti-clotting medication; and cholestyramine (Questran) and colestipol (Colestid), used to treat high cholesterol. Gum disease causes bone loss because these harmful bacteria in our mouths force our bodies to defend against them. The bacteria produce toxins and enzymes under the gum-line, causing a chronic infection.

In a further embodiment, the present invention provides methods and therapeutic agents for treating diseases or disorders associated with abnormal or unwanted bone growth. For example, patients having the disease known as Fibrodysplasia Ossificans Progressiva (FOP) grow an abnormal "second skeleton" that prevents any movement. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma. Examples of these therapeutic agents include, but are not limited to, ActRII polypeptides that antagonize function of an ActRII ligand (e.g., BMP7), compounds that disrupt interaction between an ActRII and its ligand (e.g., BMP7), and antibodies that specifically bind to an ActRII receptor such that an ActRII ligand (e.g., BMP7) cannot bind to the ActRII receptor.

In other embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof an ActRII polypeptide.

In one specific embodiment, the present invention relates to methods and compounds for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass.

In other embodiments, the subject ActRII polypeptides can be used to form pharmaceutical compositions that can be beneficially used to prevent, treat, or alleviate symptoms of a host of diseases involving neurodegeneration. While not wishing to be bound by any particular theory, the subject ActRII polypeptides may antagonize the inhibitory feedback mechanism mediated through the type I receptor ALK7, thus allowing new neuronal growth and differentiation. The subject ActRII polypeptides as pharmaceutical compositions can be beneficially used to prevent, treat, or alleviate symptoms of diseases with neurodegeneration, including Alzheimer's Disease (AD), Parkinson's Disease (PD), Amyotrophic Lateral Sclerosis (ALS), and Huntington's disease (HD).

AD is a chronic, incurable, and unstoppable central nervous system (CNS) disorder that occurs gradually, resulting in memory loss, unusual behavior, personality changes, and a decline in thinking abilities. These losses are related to the death of specific types of brain cells and the breakdown of connections between them. AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses. AD patients most commonly die from pneumonia, 8 to 20 years from disease onset.

PD is a chronic, incurable, and unstoppable CNS disorder that occurs gradually and results in uncontrolled body movements, rigidity, tremor, and gait difficulties. These motor system problems are related to the death of brain cells in an area of the brain that produces dopamine, a chemical that helps control muscle activity. In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden. People with PD usually die from pneumonia.

ALS, also called Lou Gehrig's disease (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

The causes of these neurological diseases have remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

HD is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing. The rate of disease progression and the age of onset vary from person to person.

Tay-Sachs disease and Sandhoff disease are glycolipid storage diseases caused by the lack of lysosomal β-hexosaminidase (Gravel et al., in The Metabolic Basis of Inherited Disease, eds. Scriver et al., McGraw-Hill, New York, pp. 2839-2879, 1995). In both disorders, GM2 ganglioside and related glycolipid substrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., Hum. Mol. Genet. 6: 1879-1885, 1997).

It is well known that apoptosis plays a role in AIDS pathogenesis in the immune system. However, HIV-1 also induces neurological disease. Shi et al. (J. Clin. Invest. 98: 1979-1990, 1996) examined apoptosis induced by HIV-1 infection of the central nervous system (CNS) in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats.

The subject ActRII polypeptides are also useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium *Mycobacterium leprae*, which attacks the peripheral nerves of affected people. According to statistics gathered by the World Health Organization, an estimated 1.15 million people have leprosy worldwide.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic—no known cause can be found. The most common of the inherited peripheral neuropathies in the United States is Charcot-Marie-Tooth disease, which affects approximately 125,000 persons.

Another of the better known peripheral neuropathies is Guillain-Barre syndrome, which arises from complications associated with viral illnesses, such as cytomegalovirus, Epstein-Barr virus, and human immunodeficiency virus (HIV), or bacterial infection, including *Campylobacter jejuni* and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the peripheral nervous system (PNS) and the central nervous system (CNS), as well as other body tissues.

Other PNS diseases treatable with the subject ActRII polypeptides include: Brachial Plexus Neuropathies (diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, 6th ed, pp 1351-2); Diabetic Neuropathies (peripheral, autonomic, and cranial nerve disorders that are associated with diabetes mellitus). These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy (see Adams et al., Principles of Neurology, 6th ed, p 1325); mononeuropathies (disease or trauma involving a single peripheral nerve in isolation, or out of proportion to evidence of diffuse peripheral nerve dysfunction). Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions); Neuralgia (intense or aching pain that occurs along the course or distribution of a peripheral or cranial nerve); Peripheral Nervous System Neoplasms (neoplasms which arise from peripheral nerve tissue. This includes neurofibromas; Schwannomas; granular cell tumors; and malignant peripheral nerve sheath tumors. See DeVita Jr et al., Cancer: Principles and Practice of Oncology, 5th ed, pp 1750-1); Nerve Compression Syndromes (mechanical compression of nerves or nerve roots from internal or external causes. These may result in a conduction block to nerve impulses, due to, for example, myelin sheath dysfunction, or axonal loss. The nerve and nerve sheath injuries may be caused by ischemia; inflammation; a direct mechanical effect; or Neuritis (a general term indicating inflammation of a peripheral or cranial nerve). Clinical manifestation may include pain; paresthesias; paresis; or hyperthesia; Polyneuropathies (diseases of multiple peripheral nerves). The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance.

7. Pharmaceutical Compositions

In certain embodiments, compounds (e.g., ActRII polypeptides) of the present invention are formulated with a pharmaceutically acceptable carrier. For example, an ActRII polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neuron), for example, a site having a tissue damage. Topical administration may be suitable for wound healing and tissue repair. Therapeutically useful agents other than the ActRII polypeptides which may also optionally be included in the composition as described above, may alternatively or additionally, be administered simultaneously or sequentially with the subject compounds (e.g., ActRII polypeptides) in the methods of the invention.

In certain embodiments, compositions of the present invention may include a matrix capable of delivering one or more therapeutic compounds (e.g., ActRII polypeptides) to a target tissue site (e.g., bone, cartilage, muscle, fat or neuron), providing a structure for the developing tissue and optimally capable of being resorbed into the body. For example, the matrix may provide slow release of the ActRII polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., an ActRII polypeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more ActRII polypeptides in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRII polypeptides). The various factors include, but are not limited to, amount of bone weight desired to be formed, the site of bone damage, the condition of the damaged bone, the size of a wound, type of damaged tissue, the patient's age, sex, and diet, the severity of any infection, time of administration, and other clinical factors. Optionally, the dosage may vary with the type of matrix used in the reconstitution and the types of compounds in the composition. The addition of other known growth factors to the final composition, may also effect the dosage. Progress can be monitored by periodic assessment of bone growth and/or repair, for example, X-rays, histomorphometric determinations, and tetracycline labeling.

In certain embodiments of the invention, one or more ActRII polypeptides can be administered, together (simultaneously) or at different times (sequentially or overlapping). In addition, ActRII polypeptides can be administered with another type of therapeutic agents, for example, a cartilage-inducing agent, a bone-inducing agent, a muscle-inducing agent, a fat-reducing, or a neuron-inducing agent. The two types of compounds may be administered simultaneously or at different times. It is expected that the ActRII polypeptides of the invention may act in concert with or perhaps synergistically with another therapeutic agent.

In a specific example, a variety of osteogenic, cartilage-inducing and bone-inducing factors have been described, particularly bisphosphonates. See e.g., European Patent Application Nos. 148,155 and 169,016. For example, other factors that can be combined with the subject ActRII polypeptides include various growth factors such as epidermal growth factor (EGF), platelet derived growth factor (PDGF), transforming growth factors (TGF-α and TGF-β, and insulin-like growth factor (IGF).

In certain embodiments, the present invention also provides gene therapy for the in vivo production of ActRII polypeptides. Such therapy would achieve its therapeutic effect by introduction of the ActRII polynucleotide sequences into cells or tissues having the disorders as listed above. Delivery of ActRII polynucleotide sequences can be achieved using a recombinant expression vector such as a chimeric virus or a colloidal dispersion system. Preferred for therapeutic delivery of ActRII polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody.

Those of skill in the art will recognize that specific polynucleotide sequences can be inserted into the retroviral genome or attached to a viral envelope to allow target specific delivery of the retroviral vector containing the ActRII polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRII polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Generation of ActRIIB Mutants

Applicants generated a series of mutations in the extracellular domain of ActRIIB and produced these mutant proteins as soluble fusion proteins between extracellular ActRIIB and an Fc domain. A co-crystal structure of Activin and extracellular ActRIIB did not show any role for the final (C-terminal) 15 amino acids (referred to as the "tail" herein) of the extracellular domain in ligand binding. This sequence failed to resolve on the crystal structure, suggesting that these residues are present in a flexible loop that did not pack uniformly in the crystal. Thompson et al. EMBO J. 2003 Apr. 1;22(7):1555-66. This sequence is also poorly conserved between ActRIIB and ActRIIA. Accordingly, these residues were omitted in the basic, or background, ActRIIB-Fc fusion construct. Additionally, position 64 in the background form is occupied by an alanine, which is generally considered the "wild type" form, although a A64R allele occurs naturally. Thus, the background ActRIIB-Fc fusion has the sequence (Fc portion underlined)(SEQ ID NO:14):

SGRGEAETRECIYYNANWELERTNQSGLERCEGEQDKRLHGYASWANSSGTIELVK

KGCWLDDFNCYDRQECVATEENPQVYFCCCEGNFCNERFTHLPEAGGGTHTCPPCP

APELLGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPVPIEKTISKAKGQP

REPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

Surprisingly, as discussed below, the C-terminal tail was found to enhance activin and GDF-11 binding, thus a preferred version of ActRIIB-Fc has a sequence (Fc portion underlined)(SEQ ID NO:15):

SGRGEAETRECIYYNANWELERTNQSGLERCEGEQDKRLHCYASWANSSGTIELVK

KGCWLDDFNCYDRQECVATEENPQVYFCCCEGNFCNERFTHLPEAGGPEVTYEPPP

TAPTGGGTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKA

LPVPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSL

SLSPGK

Various mutations were introduced into the background ActRIIB-Fc protein. Mutations were generated in ActRIIB extracellular domain by PCR mutagenesis. After PCR, fragments were purified thru Qiagen column, digested with SfoI and AgeI and gel purified. These fragments were ligated into expression vector pAID4 such that upon ligation it created fusion chimera with human IgG1. Upon transformation into *E. coli* DH5 alpha, colonies were picked and DNAs were isolated. All mutants were sequence verified.

All of the mutants were produced in HEK293T cells by transient transfection. In summary, in a 500 ml spinner, HEK293T cells were set up at $6 \times 10^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

All the mutants were purified over protein A column and eluted with low pH (3.0) glycine buffer. After neutralization, these were dialyzed against PBS.

Mutants were also produced in CHO cells by similar methodology.

Mutants were tested in binding assays and bioassays described below. Proteins expressed in CHO cells and HEK293 cells were indistinguishable in the binding assays and bioassays.

Example 2

GDF-11 and Activin A Binding

Binding of ActRIIB-Fc proteins was tested in a BiaCore™ assay.

GDF-11 or Activin A ("ActA") were immobilized on a BiaCore CM5 chip using standard amine coupling procedure. The ActRIIB-Fc mutant or wild-type protein was loaded onto the system, and binding was measured. Results are summarized in Table 1, below.

TABLE 1

Soluble ActRIIB-Fc binding to GDF11 and Activin A (BiaCore assay) 9779575_1

| ActRIIB | ActA | GDF11 |
|---|---|---|
| WT (64A) | KD = 1.8e-7M (+) | KD = 2.6e-7M (+) |
| WT (64R) | na | KD = 8.6e-8M (+++) |
| +15tail | KD ~2.6 e-8M (+++) | KD = 1.9e-8M (++++) |
| E37A | * | * |
| R40A | – | – |
| D54A | – | * |
| K55A | ++ | * |
| R56A | * | * |
| K74A | KD = 4.35e-9 M +++++ | KD = 5.3e-9M +++++ |
| K74Y | * | — |
| K74F | * | — |
| K74I | * | — |
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | — |
| F82A | ++ | – |

* No observed binding
— <1/5 WT binding
- ~1/2 WT binding
+ WT
++ <2x increased binding
+++ ~5x increased binding
++++ ~10x increased binding
+++++ ~40x increased binding As shown in Table 1, mutations had varying effects on ligand binding. The addition of the C-terminal 15 amino acids of the extracellular domain caused a substantial increase in binding affinity for both Activin A and GDF-11, and it is expected that this effect will translate to essentially all of the other mutations. Other mutations caused an overall increase in ligand binding affinity, including the naturally occurring allele A64R and K74A. The R40A mutation caused a moderate decrease in binding affinity for both Activin A and GDF-11. Many mutations abolished detectable binding to Activin A and GDF-11, including: E37A, R56A, W78A, D80K, D80R, D80A, D80G, D80F, D80M and D80N. Certain mutations caused a shift in selectivity. The following mutations caused an increase in the ratio of GDF-11 to Activin A binding: K74Y, K74F, K74I and D80I. The following mutations caused a decrease in the ratio of GDF-11 to Activin A binding: D54A, K55A, L79A and F82A.

Example 3

Bioassay for GDF-11 and Activin-mediated Signaling

An A-204 Reporter Gene Assay was used to evaluate the effects of ActRIIB-Fc proteins on signaling by GDF-11 and Activin A. Cell line: Human Rhabdomyosarcoma (derived from muscle). Reporter vector: pGL3(CAGA)12 (Described in Dennler et al, 1998, EMBO 17: 3091-3100.) See FIG. 5. The CAGA12 motif is present in TGF-Beta responsive genes (PAI-1 gene), so this vector is of general use for factors signaling through Smad2 and 3.

Day 1: Split A-204 cells into 48-well plate.

Day 2: A-204 cells transfected with 10 ug pGL3(CAGA)12 or pGL3(CAGA)12(10 ug)+pRLCMV (1 ug) and Fugene.

Day 3: Add factors (diluted into medium+0.1% BSA). Inhibitors need to be preincubated with Factors for 1 hr before adding to cells. 6 hrs later, cells rinsed with PBS, and lyse cells.

This is followed by a Luciferase assay. In the absence of any inhibitors, Activin A showed 10 fold stimulation of reporter gene expression and an ED50 ~2 ng/ml. GDF-11: 16 fold stimulation, ED50: ~1.5 ng/ml.

As shown in FIG. 16, wild-type (background A64) ActRIIB-Fc inhibits GDF-11 signaling in the A-204 Reporter Gene Assay. The background A64 construct showed an inhibitory effect on GDF-11 activity. The A64K mutation (also a naturally occurring form) caused a substantial increase in GDF-11 inhibition, and a combination of the A64K mutation with the addition of the 15 C-terminal amino acids of the extracellular domain (the 15 amino acid "tail") produced an even more potent inhibitor of GDF-11 activity. As shown in FIG. 17, the background A64 construct showed an inhibitory effect on Activin A activity. The K74A mutation caused a substantial increase in Activin A inhibition. A control sample lacking Activin A showed no activity.

These data from the bioassay system correlate well with the binding assays shown in Table 1 and demonstrate that the effects of the various mutations translate to a biological system.

Example 4

ActRIIA-Fc Fusion Proteins

As shown in FIG. 14, ActRIIA and ActRIIB are highly conserved. Accordingly, most of the mutations tested in ActRIIB are expected to have similar effects in ActRIIA. Thus, a background ActRIIA-Fc fusion may be constructed with the following sequence (Fc portion underlined)(SEQ ID NO:16):

```
AILGRSETQECLFFNANWEKDRTNQTGVEPCYGDKDKRRHCFATWKNISGSIEIVKQ
GCWLDDINCYDRTDCVEKKDSPEVYFCCCEGNMCNEKFSYFPEMGGGTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPVPIEKTISKAKGQPRE
PQVYTLPPSREEMTKNQVSLTCLVKGFYPSDIAVEWESNGOPENNYKTTPPVLDSDG
SFFLYSKLTVDKSRWQQGNVFSCSVMHEALHNHYTQKSLSLSPGK
```

As discussed below, the C-terminal tail was found to enhance activin and GDF-11 binding, thus a preferred version of ActRIIA-Fc has a sequence (Fc portion underlined)(SEQ ID NO:17):

```
AILGRSETQECLFFNANWEKDRTNQTGVEPCYGDKDKRRHCFATWKNISGSIEIVKQ
GCWLDDLNCYDRTDCVEKKDSPEVYFCCCEGNMCNEKFSYFPEMEVTQPTSNPVTP
KPPGGGTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKAL
PVPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLS
LSPGK
```

Additional mutations, corresponding to those made in ActRIIB, may be made in the background version of ActRIIA or the "tail" version of ActRIIA. The correspondence between ActRIIB and ActRIIA mutations is shown in Table 2 below.

| ActRIIB Mutant | Functional Effect | Corresponding ActRIIA Mutant |
|---|---|---|
| WT (64A) | Background. | WT is K65, so K65A mutation is expected to decrease binding to all ligands. |
| WT (64R) | Increase binding to all ligands. | K65, background. |
| +15tail | Increase binding to all ligands. | +15 tail |
| E37A | Eliminate detectable binding to all ligands. | E38A |
| R40A | Decrease binding to all ligands. | R41A |
| D54A | Decrease GDF-11/Activin binding ratio. | D55A |
| K55A | Decrease GDF-11/Activin binding ratio. | K56A |
| R56A | Eliminate detectable binding to all ligands. | R57A |
| K74A | Increase binding to all ligands. | K75A |
| K74Y | Increase GDF-11/Activin binding ratio. | K75Y |
| K74F | Increase GDF-11/Activin binding ratio. | K75F |
| K74I | Increase GDF-11/Activin binding ratio. | K75I |
| W78A | Eliminate detectable binding to all ligands. | W79A |
| L79A | Decrease GDF-11/Activin binding ratio. | L80A |
| D80K | Eliminate detectable binding to all ligands. | D81K |
| D80R | Eliminate detectable binding to all ligands. | D81R |
| D80A | Eliminate detectable binding to all ligands. | D81A |
| D80F | Eliminate detectable binding to all ligands. | D81F |
| D80G | Eliminate detectable binding to all ligands. | D81G |
| D80M | Eliminate detectable binding to all ligands. | D81M |
| D80N | Eliminate detectable binding to all ligands. | D81N |
| D80I | Increase GDF-11/Activin binding ratio. | D81I |
| F82A | Decrease GDF-11/Activin binding ratio. | I83A |

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. An isolated polypeptide comprising an altered GDF11-binding domain of an ActRII receptor having an increased selectivity for GDF11 versus activin relative to a GDF11-binding domain of a wild-type receptor, wherein the amino acid sequence of the altered GDF11-binding domain comprises: (i) the amino acid sequence of SEQ ID NO: 1 wherein the amino acid residue at position 56 or 62 has been altered relative to the sequence of SEQ ID NO: 1, or (ii) the amino acid sequence of SEQ ID NO: 2 wherein the amino acid residue at position 56 or 62 has been altered relative to the sequence of SEQ ID NO: 2.

2. The polypeptide of claim 1, wherein the altered binding domain has a ratio of $K_d$ for activin binding to $K_d$ for GDF11 binding that is at least 2 fold greater for the altered binding domain relative to the ratio for the GDF11-binding domain of a wild-type receptor.

3. The polypeptide of claim 1, wherein the altered binding domain has a ratio of $K_d$ for activin binding to $K_d$ for GDF11 binding that is at least 5 fold greater for the altered binding domain relative to the ratio for the GDF11-binding domain of a wild-type receptor.

4. The polypeptide of claim 1, wherein the altered binding domain has a ratio of $k_d$ for activin binding to $k_d$ for GDF11 binding that is at least 10 fold greater for the altered binding domain relative to the ratio for the GDF11-binding domain of a wild-type receptor.

5. The polypeptide of claim 1, wherein the altered binding domain has a ratio of $k_d$ for activin binding to $k_d$ for GDF11 binding that is at least 100 fold greater for the altered binding domain relative to the ratio for the GDF11-binding domain of a wild-type receptor.

6. The polypeptide of claim 1, wherein the altered binding domain has a ratio of $IC_{50}$ for inhibiting activin to $IC_{50}$ for inhibiting GDF11 that is at least 2 fold greater for the altered binding domain than the GDF11-binding domain of a wild-type receptor.

7. The polypeptide of claim 1, wherein the altered binding domain has a ratio of $IC_{50}$ for inhibiting activin to $IC_{50}$ for inhibiting GDF11 that is at least 5 fold greater for the altered binding domain than the GDF11-binding domain of a wild-type receptor.

8. The polypeptide of claim 1, wherein the altered binding domain has a ratio of $IC_{50}$ for inhibiting activin to $IC_{50}$ for inhibiting GDF11 that is at least 10 fold greater for the altered binding domain than the GDF11-binding domain of a wild-type receptor.

9. The polypeptide of claim 1, wherein the altered binding domain has a ratio of $IC_{50}$ for inhibiting activin to $IC_{50}$ for inhibiting GDF11 that is at least 100 fold greater for the altered binding domain than the GDF11-binding domain of a wild-type receptor.

10. The polypeptide of claim 1, which inhibits GDF11 with an $IC_{50}$ at least 2 times less than the $IC_{50}$ of the polypeptide for inhibiting activin.

11. The polypeptide of claim 1, which inhibits GDF11 with an $IC_{50}$ at least 5 times less than the $IC_{50}$ of the polypeptide for inhibiting activin.

12. The polypeptide of claim 1, which inhibits GDF11 with an $IC_{50}$ at least 10 times less than the $IC_{50}$ of the polypeptide for inhibiting activin.

13. The polypeptide of claim 1, which inhibits GDF11 with an $IC_{50}$ at least 100 times less than the $IC_{50}$ of the polypeptide for inhibiting activin.

14. The polypeptide of claim 1, wherein the GDF11 polypeptide is a fusion protein.

15. The polypeptide of claim 14, wherein said altered GDF11-binding domain of an ActRII receptor is fused to an IgG Fc domain.

16. The polypeptide of claim 15, wherein said IgG Fc domain comprises one or more mutations.

17. The polypeptide of claim 16, wherein the Fc domain has reduced ability to bind to the Fcγ receptor relative to a wild-type Fc domain.

18. The polypeptide of claim 16, wherein the Fc domain has increase ability to bind to the MHC class I-related Fc-receptor (FcRN) relative to a wild-type Fc domain.

19. The polypeptide of claim 15, wherein the Fc domain has a mutation at residues selected from the group consisting of: Asp-265, lysine 322, and Asn-434.

20. The polypeptide of claim 16, wherein the mutation is shown in FIG. 12.

21. The polypeptide of claim 15, wherein the IgG Fc domain has an amino acid sequence as set forth in SEQ ID NO: 13.

22. The polypeptide of claim 1, wherein the altered GDF11-binding domain comprises the amino acid sequence of SEQ ID NO: 1 wherein the amino acid at position 56 has been changed to a tyrosine.

23. The polypeptide of claim 1, wherein the altered GDF11-binding domain comprises the amino acid sequence of SEQ ID NO: 1 wherein the amino acid at position 56 has been changed to a phenylalanine.

24. The polypeptide of claim 1, wherein the altered GDF11-binding domain comprises the amino acid sequence of SEQ ID NO: 1 wherein the amino acid at position 56 has been changed to a isoleucine.

25. The polypeptide of claim 1, wherein the altered GDF11-binding domain comprises the amino acid sequence of SEQ ID NO: 1 wherein the amino acid at position 62 has been changed to an isoleucine.

26. The polypeptide of claim 1, wherein the altered GDF11-binding domain comprises the amino acid sequence of SEQ ID NO: 2 wherein the amino acid at position 56 has been changed to a tyrosine.

27. The polypeptide of claim 1, wherein the altered GDF11-binding domain comprises the amino acid sequence of SEQ ID NO: 2 wherein the amino acid at position 56 has been changed to a phenylalanine.

28. The polypeptide of claim 1, wherein the altered GDF11-binding domain comprises the amino acid sequence of SEQ ID NO: 2 wherein the amino acid at position 56 has been changed to a isoleucine.

29. The polypeptide of claim 1, wherein the altered GDF11-binding domain comprises the amino acid sequence of SEQ ID NO: 2 wherein the amino acid at position 62 has been changed to an isoleucine.

* * * * *